(12) United States Patent
Yoshinari et al.

(10) Patent No.: US 6,907,352 B2
(45) Date of Patent: Jun. 14, 2005

(54) MASS SPECTROMETRIC DATA ANALYZING METHOD, MASS SPECTROMETRIC DATA ANALYZING APPARATUS, MASS SPECTROMETRIC DATA ANALYZING PROGRAM, AND SOLUTION OFFERING SYSTEM

(75) Inventors: Kiyomi Yoshinari, Hitachi (JP); Kinya Kobayashi, Hitachi (JP); Lee Chahn, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 171 days.

(21) Appl. No.: 10/253,481

(22) Filed: Sep. 25, 2002

(65) Prior Publication Data

US 2003/0236634 A1 Dec. 25, 2003

(30) Foreign Application Priority Data

Jun. 25, 2002 (JP) ........................ 2002-185072

(51) Int. Cl.[7] .................. G01N 31/00; G06F 19/00
(52) U.S. Cl. ................... 702/23; 702/27; 250/281; 250/282; 250/283; 250/252.1
(58) Field of Search .................. 702/23, 27; 250/281, 250/282, 283, 252.1

(56) References Cited

U.S. PATENT DOCUMENTS

| | | | |
|---|---|---|---|
| 5,932,384 A | 8/1999 | Mitsumori et al. | |
| 6,107,623 A1 | 8/2002 | Bateman et al. | |
| 6,483,109 B1 | 11/2002 | Reinhold et al. | |
| 6,624,408 B1 | 9/2003 | Franzen | |
| 6,717,130 B2 * | 4/2004 | Bateman et al. | |
| 6,745,134 B2 * | 6/2004 | Kobayashi et al. | 702/27 |
| 2003/0236636 A1 * | 12/2003 | Yoshinari et al. | 702/27 |
| 2004/0111228 A1 * | 6/2004 | Kobayashi et al. | 702/81 |

FOREIGN PATENT DOCUMENTS

| | | |
|---|---|---|
| JP | 08180830 A | 7/1996 |
| JP | 2002110081 | 4/2002 |

* cited by examiner

*Primary Examiner*—Nikita Wells
(74) *Attorney, Agent, or Firm*—Dickstein Shapiro Morin & Oshinsky LLP

(57) ABSTRACT

A main object is to cope with an unknown structure substance thereby to identify the structure of a parent ion highly precisely and to derive a supposed structure. A method for analyzing mass spectrometric data is disclosed, which: acquires mass spectrometric data on an ionized sample and dissociated ions dissociated from the sample as a parent ion; derives dissociated ion candidates by analyzing the molecular orbits on the candidates of the structures of the parent ion; and displays the analytical results of the parent ion candidates and the dissociated ion candidates and compares the data of the dissociated ion candidates and the data of dissociated ions actually measured, to evaluate the structures of the parent ion candidates.

15 Claims, 20 Drawing Sheets

RESERPINE

MASS SPECTROMETRIC DATA ANALYZING METHOD, MASS SPECTROMETRIC DATA ANALYZING APPARATUS, MASS SPECTROMETRIC DATA ANALYZING PROGRAM, AND SOLUTION OFFERING SYSTEM

BACKGROUND OF THE INVENTION

1. Field of the Invention

The present invention relates to an analytical method for analyzing mass spectrometric data, a mass spectrometric data analyzing apparatus, amass spectrometric data analyzing program, and a solution offering system.

2. Description of Related Art

There has increasing a mass spectrometer which has a tandem mass spectrometric function to dissociate a substance (or a parent ion) to improve the identification precision of the substance from mass spectrometric data obtained by the mass spectrometer, and to make a further mass spectrometry of the dissociated ions. The method for identifying the parent ion and for deriving the supposed structure of the parent ion with the mass spectrometric data (i.e., MS data) of the parent ion and the mass spectrometric data (i.e., $MS^2$ data) of the dissociated ions is mainly classified into the following methods:

(1) A database retrieving method of the mass spectrometric data (i.e., the MS data) of the parent ion;
(2) A database retrieving method of the mass spectrometric data (i.e., the MS data and the $MS^2$ data) of the parent ion and the dissociated ions; and
(3) A method for suppositions based on the mass spectrometric data (i.e., the MS data and the $MS^2$ data) of the parent ion and the dissociated ions but not depending on the database.

On example of the related art (2) is disclosed in JP-A-8-124519. In this disclosure, for the individual peaks of the mass spectrum or mass spectrometric data, the candidates for the ion species corresponding to the peak mass are extracted with reference to the peak database, and the candidates for the eliminated radicals corresponding to the elimination mass are extracted with reference to the elimination radical database. Moreover, the candidates for the parent ion are determined with reference to the structure constructing database which is stored with rules for constructing the parent ion from the dissociated ions and the eliminated radicals.

In an amino acid configuration analysis supporting software "SeqMS" developed by Ohsaka University, on the other hand, the related art (3) is exemplified by identifying about ten amino acid configurations of peptide without resorting to the database retrieval. This software derives the amino acid configuration candidates by the statistical procedures which are based on the graph theory using the weighting values of the dissociation probability determined empirically (or experimentally) from the mass spectrometric data of the peptide ions and their dissociated ions.

When the database retrievals of the related arts (1) and (2) are used as the method for identifying the parent ion and for deriving the supposed structure of the parent ion by the mass spectrometric data (i.e., the MS data) of the parent ion and the mass spectrometric data (i.e., the $MS^2$ data) of the dissociated ions, however, the parent ion is difficult to identify, and the supposed structure is difficult to derive, because no data is present in the database for a substance having an unknown structure.

When the statistical processing based on the graph theory and the information processing of a numerical arrangement are performed as the method without resorting to the database retrieval, as disclosed in the related art (3), on the other hand, it is the current practice that the identification precision of the parent ion is seriously lowered to one half or less.

Therefore, a main object of the present invention is to cope with an unknown structure substance thereby to identify the structure of a parent ion highly precisely and to derive a supposed structure.

SUMMARY OF THE INVENTION

As the means of the present invention for solving the aforementioned problems, the structures of a parent ion or a sample and dissociated ions produced from the parent ion are derived/displayed highly precisely by acquiring the mass spectrometric data of the parent ion and the dissociated ions and by performing a molecular orbit analysis by itself or in combination with molecular dynamic calculations or molecular kinetic calculations, upon the structure of the parent ion, as supposed from the mass spectrometric data. Moreover, this means can be expanded to services for offering the analytical result as a solution to a customer.

DESCRIPTION OF THE PREFERRED EMBODIMENTS (First Embodiment)

A first embodiment of the present invention will be described in detail with reference to the accompanying drawings.

Figure 1:
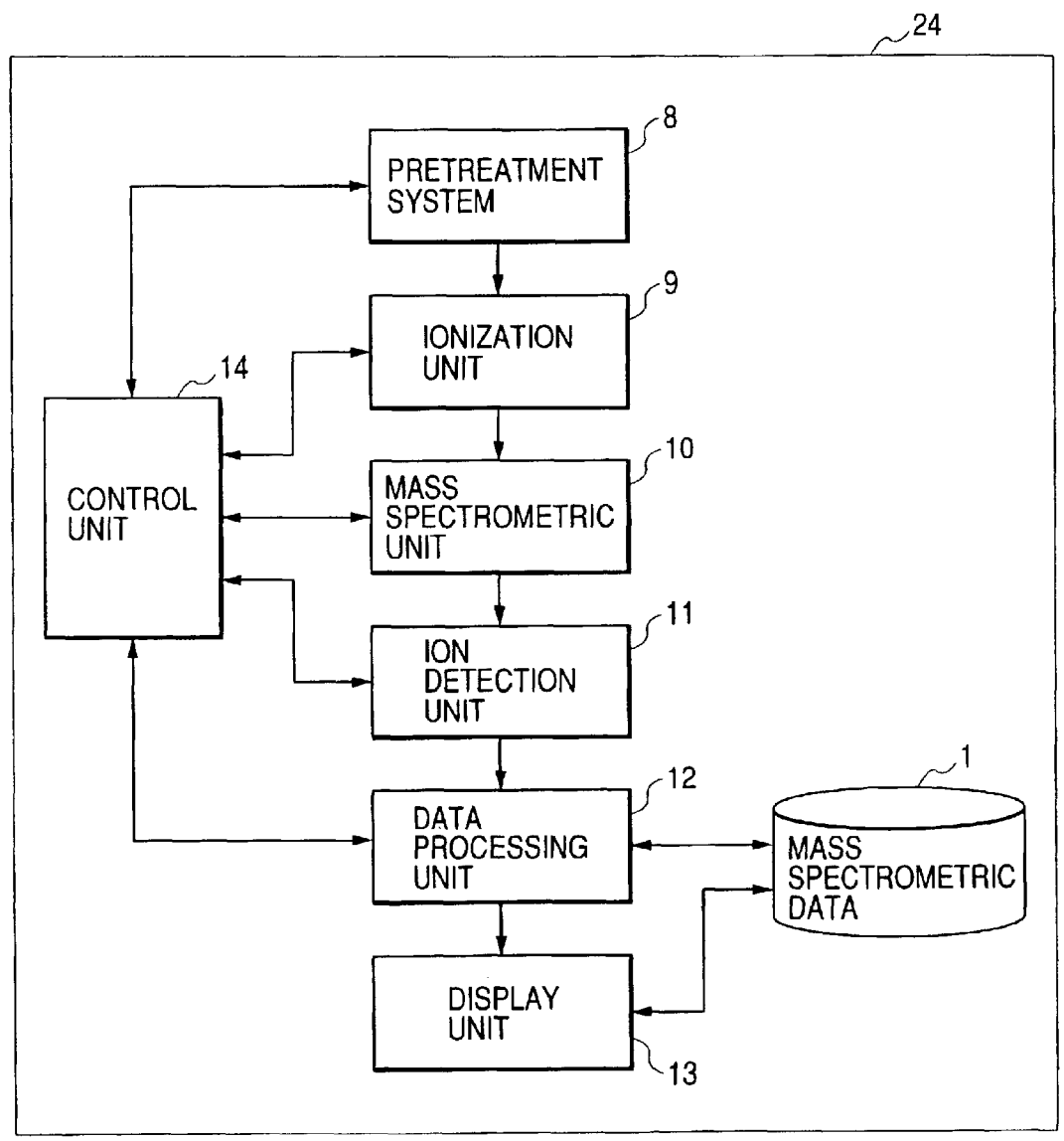
FIG. 1 is a diagram showing a construction of a mass spectrometer or a mass spectrometric data analyzing apparatus of the present invention.
Figure 2:
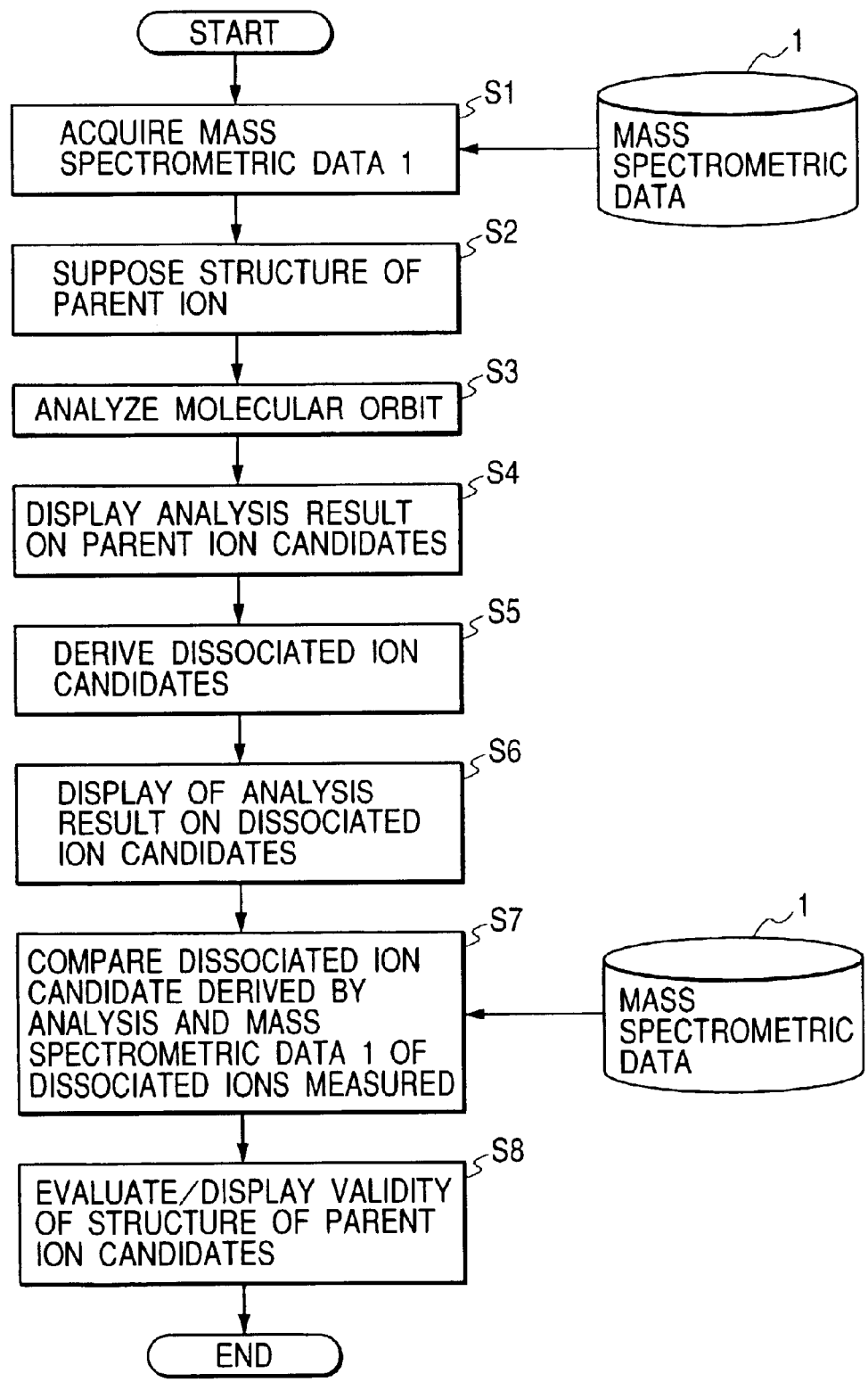
FIG. 2 is a flow chart showing a mass spectrometric data analyzing method.

FIG. 1 is a block diagram showing a construction of a mass spectrometer or a mass spectrometric data analyzing apparatus, and FIG. 2 is a flow chart showing a processing of the mass spectrometer.

The present embodiment is characterized in that a structure analysis of a sample is performed: by operating at least one of the thermal, chemical and energetic properties of a structure supposed on the basis of the mass spectrometric result of the sample, by a molecular orbit analysis; and by evaluating the validity of the supposed structure on the basis of the operation result. This processing is performed by using a mass spectrometer 24 shown in FIG. 1.

The mass spectrometer 24 or the mass spectrometric data analyzing apparatus includes: a data processing unit 12 for analyzing a molecular orbit analysis on the mass spectrometric data 1 measured on a sample to be analyzed; and a display unit 13 for displaying the analytical result. The measurement of the mass spectrometric data is made by ionizing the sample, after pretreated in a pretreatment system 8 such as a liquid chromatograph, by the well-known method in an ionization unit 9, and by detecting the ions dissociated according to the mass in a mass spectrometric unit 10, by an ion detection unit 11. This mass spectrometer 24 is generally controlled by a control unit 14. This control unit 14 controls a series of mass spectrometric procedure including the pretreatment of the sample, the ionization of the sample, the transfer and incidence of the sample ion beam obtained by the ionization, to and on the mass spectrometric unit 10, the mass separating procedure and the ion detection.

The mass spectrometric unit 10 may be provided with dissociation means for producing dissociated ions (or daughter ions) having smaller mass numbers by cleaving the ionized sample by a collision induced dissociation. The method for the mass spectrometry of the dissociated ions, too, by using the dissociation means is called the tandem mass spectrometry (or the MS/MS analysis). According to this method, information on the molecules constructing the parent ion (or the sample ion) can be acquired to suppose the structure of the parent ion on the information. This dissociation means can be exemplified by a collision cell. The collision cell is a device for producing the dissociated ions by causing an inert gas such as helium used as a buffer gas to collide against specific sample ions. The collision induced dissociation phenomenon in a low-energy region, as caused by causing the buffer gas such as the inert gas to collide against the parent ion, is thought as the thermal dissociation phenomenon, i.e., the thermochemical reaction. As another example of the dissociation means, there can be enumerated a device for producing the dissociated ions by irradiating with an infrared ray. Here, the mass spectrometer 24 need not be provided with the dissociation means when it uses only the method (the MS analysis) by which the sample is ionized and analyzed as it is. The following description will be made with an assumption that the mass spectrometer 24 includes the dissociation means and makes the tandem mass spectrometry. Therefore, an ionized sample before being dissociated shall be termed a parent ion.

The data processing unit 12 is constructed to include a CPU (Central Processing Unit), a ROM (Read Only Memory) and a RAM (Random Access Memory), and identifies the parent ion by making the molecular orbit analysis of the parent ion, as will be described, when the analytic programs for the mass spectrometric data analysis are expanded/started.

The display unit 13 can be exemplified by a CRT (Cathode-Ray Tube) display or a liquid crystal display. The display unit 13 may also be another means if it can display another data processing result to be made by the data processing unit 12.

Figure 3A:
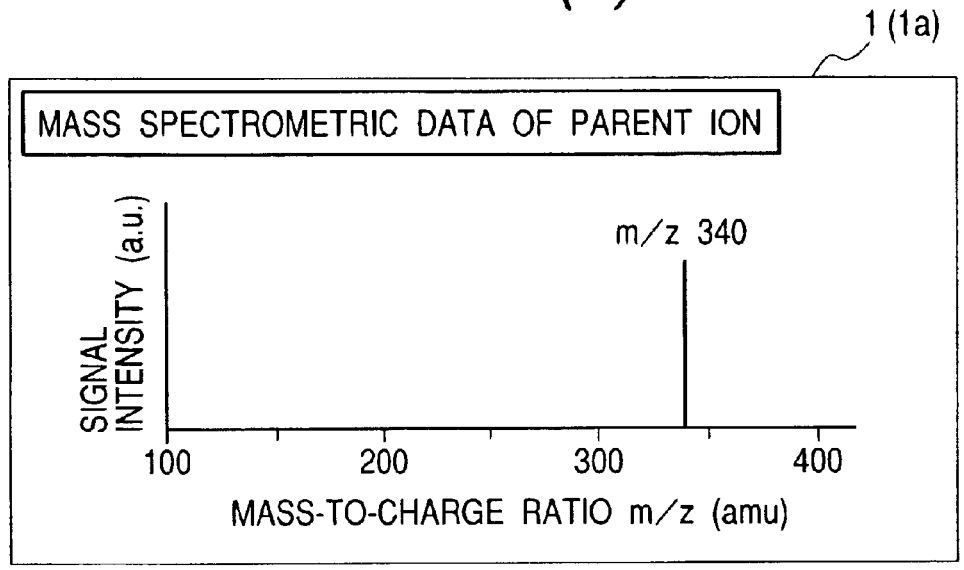
FIG. 3A is a diagram illustrating mass spectrometric data of a parent ion.
Figure 3B:
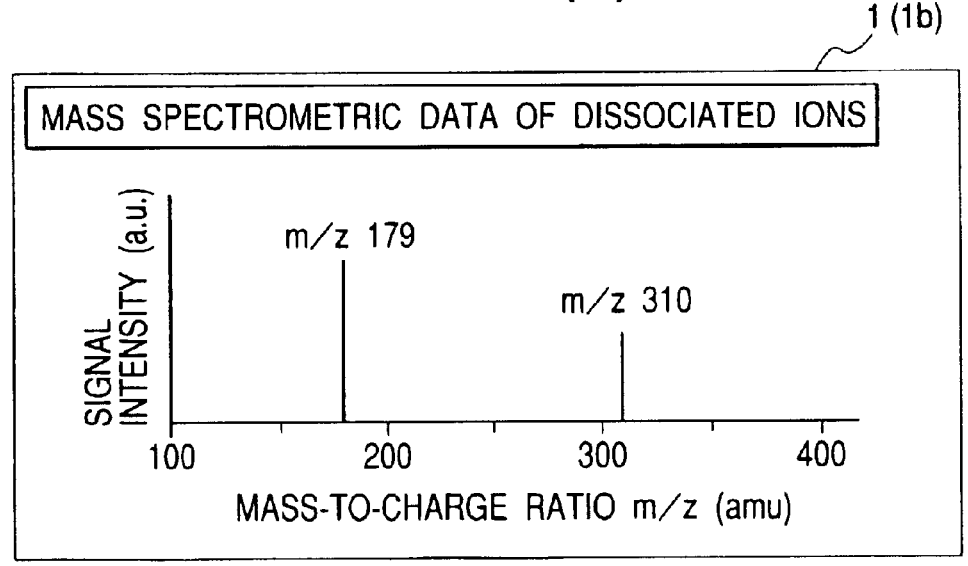
FIG. 3B is a diagram illustrating mass spectrometric data of dissociated ions.

Examples of the mass spectrometric data 1, as obtained by such mass spectrometer 24, of the parent ion and the dissociated ions are illustrated at FIGS. 3A and 3B. FIG. 3A illustrates the mass spectrometric data 1 of the parent ion and that the parent ion has a mass-to-charge ratio (as will be expressed by m/z) of 340 amu. FIG. 3B illustrates the mass spectrometric data 1 of the dissociated ions obtained by causing the parent ion to collide thereby to dissociate it, and peaks are observed at locations of m/z=179 amu and m/z=310 amu. This means that the dissociated ion of m/z=179 amu and the dissociated ion of m/z=310 amu are produced from the parent ion of m/z=340 amu by the dissociation means of the mass spectrometric unit 10 shown in FIG. 1.

The present embodiment analyzes the structure of the parent ion on the basis of the mass spectrometric data 1 obtained on such parent ion and dissociated ions. This analyzing procedure will be described with reference to the flow chart of FIG. 2. Here, the sample the structure of which is to be analyzed as the parent ion is exemplified by either a high molecule relating to a living organism such as protein, peptide or saccharides, or a low molecule having an unknown structure on a synthetic molecule such as a medicine. However, the sample should not be limited to those molecular weights or kinds.

First of all, at Step S1 of FIG. 2, the mass spectrometric data 1 on the parent ion are acquired by using the mass spectrometric unit 10. These mass spectrometric data 1 are obtained through a series of mass spectrometric procedure and composed of the mass spectrometric data of the parent ion (as will be referred to "MS data 1a" for discriminations) and the mass spectrometric data, as made by using the dissociation means, of the dissociated ions (as will also be referred to "MS$^2$ data 1b" for discriminations).

Figure 4A:
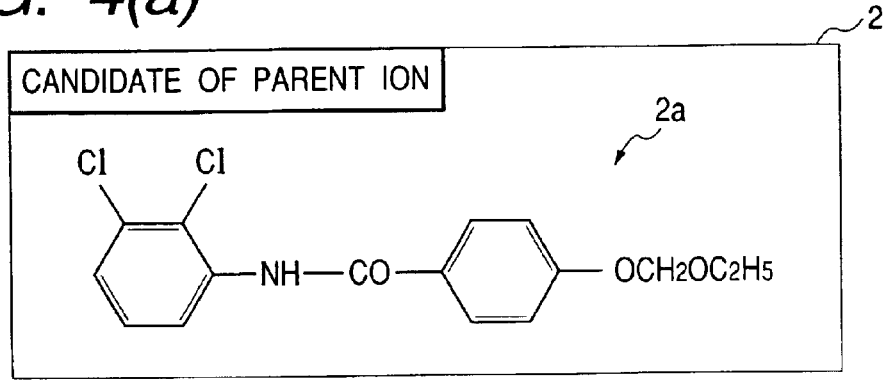
FIGS. 4A, 4B and 4C are diagrams illustrating analytical result screens.

At subsequent Step S2, the structure of the parent ion is estimated. The supposing method to be used here can be exemplified by a method for supposing the structure from the preparing procedure of the sample and a method for the user to make a coarse estimation on the basis of the mass spectrometric data 1 of the parent ion. These methods may be replaced by or used together with a method for supposing the structure of the parent ion by processing a software to list up the conceivable structures of the parent ion as candidates on the basis of the MS data 1a. The supposition of the structure of the parent ion at this stage is done for selecting the candidates for such procedures at and after Step S3 which characterize the present embodiment and is desired to list up a plurality of structures. For an easier understanding, the description will be made on the case, in which a parent ion candidate 2a having a planar structure using molecular symbols shown in FIG. 4A is to be processed. It is desired that the parent ion candidate 2a supposed is so displayed as a parent ion candidate screen 2 that its construction may be easily confirmed by the user.

On the structure of the parent ion candidate 2a supposed at the aforementioned Step, the molecular orbit is analyzed at Step S3 by calculating at least one of the thermal, chemical and energetic properties of the molecular structure. In the present embodiment, the strength of interatomic bonds is taken up as the thermal, chemical and energetic properties, and the data processing unit 12 shown in FIG. 1 uses the molecular orbit analysis to operate the strength of the interatomic bonds of the atoms constructing the parent ion candidate 2a.

Figure 4B:
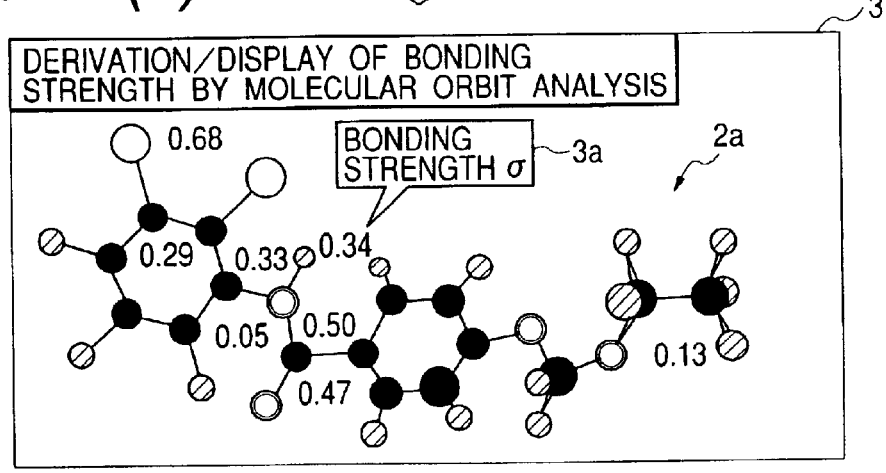
Figure 4C:
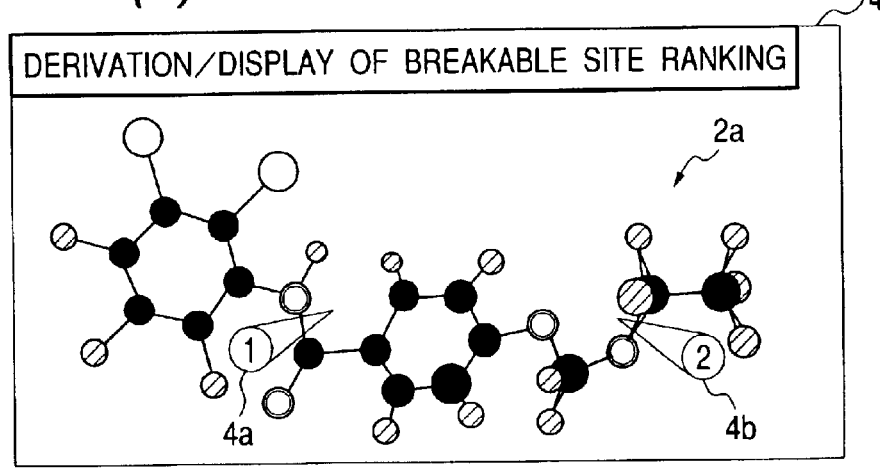

The analytical result on the parent ion candidate 2a is displayed at Step S4 in the display unit 13 (as referred to FIG. 1). The display of this case is exemplified by an analytical result screen 3, as shown in FIG. 4B. The analytical result screen 3 contains the stereoscopic structure of the parent ion candidate 2a, digits attached to a predetermined bonds, and texts 3a explaining the digits. According to this analytical result screen 3, it is easily understood from the texts 3a that the digits attached to the bonds indicate a bonding strength σ. It can also be judged that the bonds having smaller digits have a lower bonding strength σ. Here, the bonding strength σ indicates only such interatomic bonds in relative values as have relative strengths at or less than a predetermined value, but may indicate them in absolute values or all bonds in relative values or absolute values. As in an analytical result screen 4 shown in FIG. 4C, on the other hand, the bonding strengths σ may be ranked from the smaller one so that rank indications 4a and 4b indicating the ranks schematically may be displayed together with the stereoscopic structure of the parent ion candidate 2a. In this analytical result screen 4, the rank indication 4a of the lowest bonding strength σ and the rank indication 4b of the second lowest bonding strength are shown to have the digits indicating the individual ranks and the drawings connecting the digits and the bonds, so that the portion of a weak bond can be quickly confirmed.

Here, the reason why the smaller two bonding strengths σ are selected is that the structure of the parent ion is efficiently evaluated by noting the dissociated ions of higher production probabilities because the probability of those bonds being broken to produce the dissociated ions can be deemed high. The number of bonding strengths σ to be noted is different from the mass number and structure of the sample. It is, therefore, desirable that the noted number can be changed into one or more by the procedure of the data processing unit 12 (as in the following case in which the number of noted data to be indicated is plural). Moreover, the analytical result screens 3 and 4 may display the planar structure of the parent ion candidate 2a.

On the basis of the bonding strength σ a obtained by the molecular orbit analysis at Step S3, moreover, the dissociated ions, which can be predicted when the parent ion candidate 2a is dissociated into a plurality of ions, are derived as the dissociated ion candidates at Step S5. In this case, two peaks are obtained as the $MS^2$ data 1b of the dissociated ions, as illustrated in FIG. 3B. Therefore, the dissociated ion candidates are derived assuming that the bonds are broken at two portions of weak bonding strengths σ (i.e., the bonds specified by the rank indication 4a and the rank indication 4b in FIG. 4C). Here, the derivations of the dissociated ion candidates are to specify the structures of the dissociated ions at the data processing unit 12 shown in FIG. 1 and to calculate their mass-to-charge ratios (m/z).

The analytical results of the dissociated ion candidates are so displayed in the display unit 13 at Step S6 that the user may be easily able to confirm their structures and m/z values and to grasp the derivation grounds. The display is exemplified by an analytical result screen 5 shown in FIG. 5A. In the analytical result screen 5, there are displayed dissociated ion candidates 5a and 5b which show the two dissociated ions derived. The dissociated ion candidate 5a has a structure of the dissociated ion which is produced when the bond of the lowest bonding strength σ is broken, and is displayed in the analytical result screen 5 in relation to the m/z value and the derivation ground (i.e., the text "DISSOCIATED ION BY DISSOCIATIVE SITE No. 1"). The dissociated ion candidate 5b has a structure of the dissociated ion which is produced when the bond of the second lowest bonding strength σ is broken, and is displayed in the analytical result screen 5 in relation to the m/z value and the derivation ground (i.e., the text "DISSOCIATED ION BY DISSOCIATIVE SITE No. 2").

By this procedure, there has been ended the structure analysis using the molecular orbit method on the parent ion candidate 2a. At subsequent Step S7, the dissociated ion candidates 5a and 5b derived by the structure analysis and the $MS^2$ data (as referred to FIG. 3B) or the measured values of the dissociated ions are compared to output the result as a corresponding screen 6 shown in FIG. 5B. This corresponding screen 6 is a graph, in which the peaks of the m/z values of the dissociated ion candidates 5a and 5b derived by the analysis are displayed as the mass spectra over the peaks 6a and 6b of the measured values of the mass spectra obtained as the $MS^2$ data 1b, as shown in FIG. 3B. In this Figure, the m/z values of the measured values and the m/z values of the analytical result are equal so that the peaks overlap. If the m/z values of the two are different, however, the peaks are located at the different positions. This difference is a material for judging the validity of the structure which has been supposed as the candidate. Here, it is desired that the peak can discriminate whether it is the peaks 5a and 5b of the measured values or the peaks of the analyzed data. This display is exemplified by making so different the mode of thickness or color of the line indicating the peaks that may be visually discriminated.

Figure 5A:
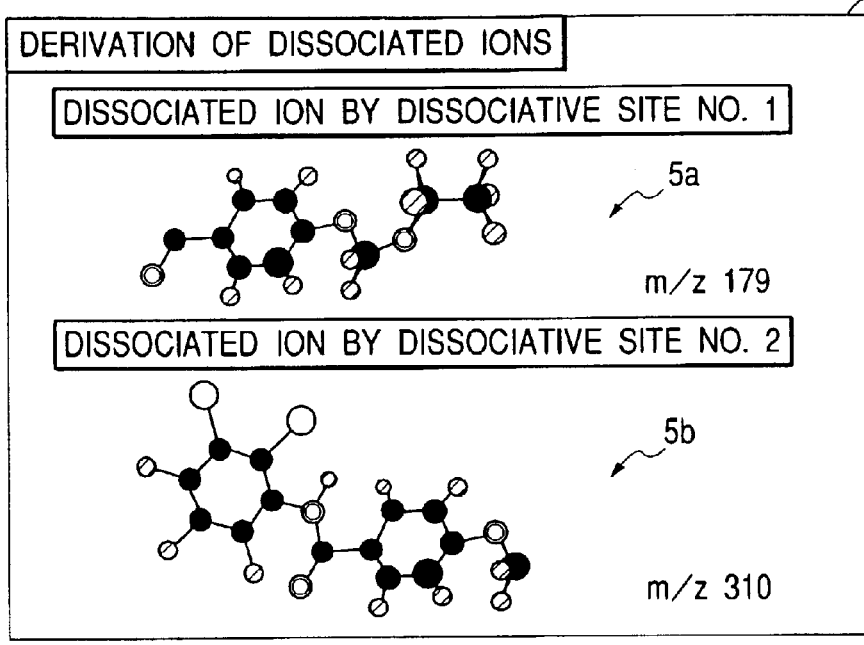
FIG. 5A is an analytical result screen.
Figure 5B:
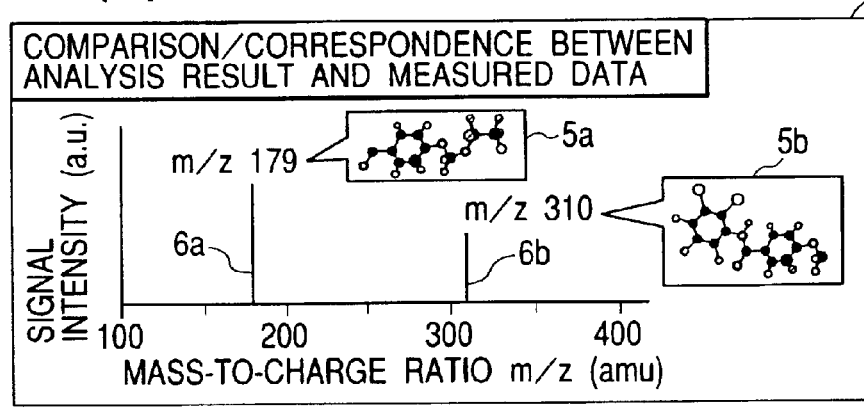
FIG. 5B is a corresponding screen.
Figure 5C:
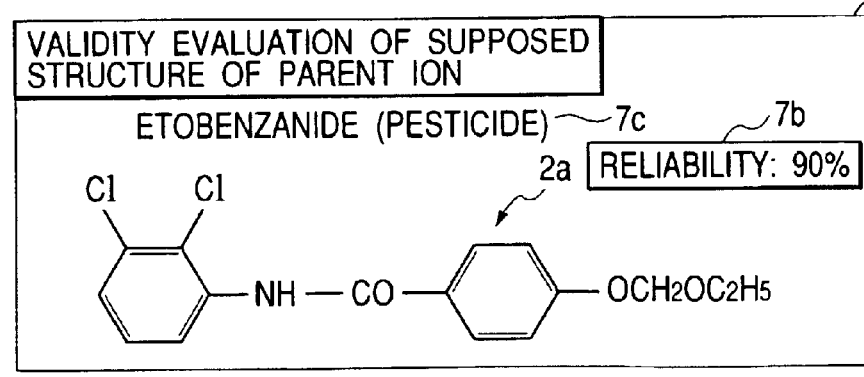
FIG. 5C is an evaluation screen.

Moreover, the validity of the structure supposed as the parent ion candidate 2a at Step S8 is evaluated, and the result is displayed as an evaluation screen 7, as shown in FIG. 5C. In the evaluation screen 7, there are displayed the parent ion candidate 2a, a reliability indication 7b and a name 7c of the sample or the parent ion. The indication 7b of the reliability may include not only the percentage indication of the reliability but also a plurality of steps A, B and C at the reliability levels. Here, the evaluation of the validity means that the consistency percentage between the measured value m/z of the dissociated ions and the calculated values of the m/z values of the dissociated ion candidates 5a and 5b is calculated so that the calculation result is indicated as the reliability of the structure of the parent ion candidate 2a supposed in advance. In this example, the m/z values of the dissociated ion candidates 5a and 5b and the actually measured m/z value of the dissociated ions are consistent so that the supposed structure of the parent ion has a reliability of 90%. By referring to this evaluation screen 7, the user can confirm not only the certainty of the parent ion candidate 2a supposed but also the name of the parent ion candidate 2a. The mass spectrometric data analyzing procedure in the mass spectrometer 24 is ended by displaying that evaluation screen 7.

If there are a plurality of candidates for the parent ion, the structure of which is to be supposed at Step S2, for all the parent ion candidates: the dissociated ion candidates are derived (at Step S5); the analytical result and the MS$^2$ data are compared (at Step S7); and the validity of each parent ion is evaluated (at Step S8). The data processing unit 12 derives the consistency percentage or the comparison result of the m/z values of the dissociated ions, and the parent ion candidates to produce those dissociated ions are ranked and displayed in the order of higher consistency percentages. Here, the consistency percentages may be indicated either in place of ranks or in numerical values together with the ranks.

Without displaying the results (at FIGS. 4B and 4C) of the molecular orbit analysis on the dissociated ion candidates of Step S6, on the other hand, it is arbitrary to display the dissociated ion candidates (i.e., the dissociated ion candidate 5a and the dissociated ion candidate 5b of FIG. 5A) which are finally obtained. In the analytical result screen 5, however, there are the results of the thermal, chemical and energetic calculations and/or the analyzed physical properties. Moreover, the data are desirably saved in files so that the user may always peruse and utilize the thermal, chemical and energetic calculation results for supplying grounds to derive the dissociated ion candidates. Alternatively, there may be given a function for the user to display, if designated. For this file saving, the data are saved in the not-shown storage device or in a recording medium.

Moreover, the analysis of the mass spectrometric data, i.e., the procedures from Step S3 to Step S8 has been described such that the mass spectrometric data can be analyzed on-site by loading the data processing unit 12 of the mass spectrometer 24 of FIG. 1 with the analyzing programs. However, the data analysis may also be executed by a computer disposed separately of the mass spectrometer 24. Here, the apparatus for analyzing the mass spectrometric data is one for making the analysis at least on the basis of the mass spectrometric data and for displaying the analytical result. Therefore, the apparatus is provided with the data processing unit 12, the display unit 13 and the associated portion of the control unit 14 as the essential elements, but does not always need to be provided with the pretreatment system 8, the ionization unit 9, the mass spectrometric unit 10 and the ion detection unit 11.

According to the present embodiment, the dissociated ions can be supposed highly precisely by calculating at least one of the thermal, chemical energetic properties on the structure of the parent ion supposed in advance. From these suppositions, the validity of the parent ion supposed in advance can be evaluated highly precisely to support the identification of the parent ion or the supposition of the structure of the parent ion highly precisely.

By providing the analytical result screen 3 using the display unit 13, moreover, the user is enabled to grasp the analytical result and the data for the ground easily.

(Second Embodiment)

A second embodiment of the present invention will be described in detail with reference to the accompanying drawings. The present embodiment relates to another display method for displaying the analytical result of the bonding strength σ obtained by the molecular orbit analysis by using the mass spectrometer 24 having the construction shown in FIG. 1. Another example for displaying the bonding strength σ a of the parent ion, as derived according to the flow chart of FIG. 2, is exemplified by the ranking indications shown in FIG. 6, by the distribution indications shown in FIG. 7, by the strength indications by color shown in FIG. 8, or by the symbol indications shown in FIG. 9. Here, the construction of the mass spectrometer 24 and the details of the individual steps of FIG. 2 are identical to the aforementioned ones of the first embodiment so that their detailed description will be omitted from the portions overlapping the aforementioned embodiment.

Figure 6:
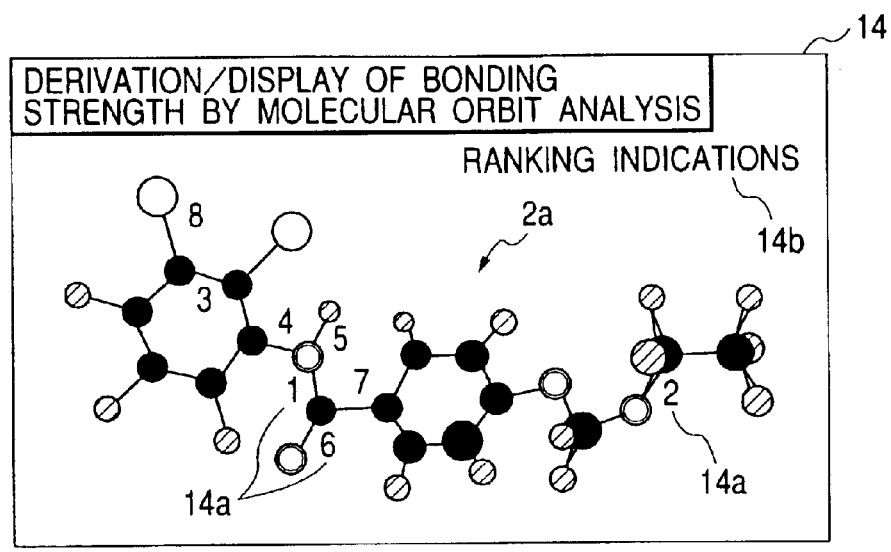
FIG. 6 is a ranking indication screen for indicating the analytical result.

FIG. 6 displays a ranking indication screen 14 as an example of the ranking indications. The ranking indication screen 14 is constructed to contain: the structure of the parent ion candidate 2a; ranking values 14a in which digits indicating the results of the bonding strengths ranked in lower orders are arranged to correspond to the bonds; and a text 14b for explaining the meanings of the ranking values 14a. According to this ranking indication screen 14, the breakableness of the bonds can be easily confirmed from the ranking values 14a. FIG. 6 illustrates an example in which digits from "1" to "8" are attached in the orders of the lower ranks, but all the bonds may be ranked.

Figure 7:
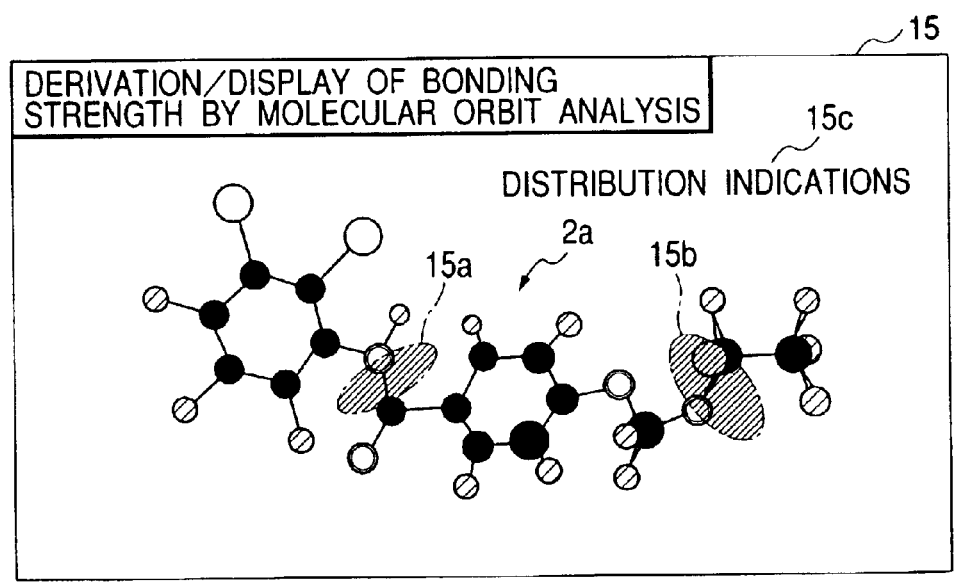
FIG. 7 is a distribution indication screen for indicating the analytical result.

FIG. 7 illustrates a distribution indication screen 15 as an example of the distribution indication. The distribution indication screen 15 is constructed to illustrate the locations of atomic bonds of lower bonding strengths as regions 15a and 15b in the stereoscopic structure of the parent ion candidate 2a, and in addition a text 15c implying the distribution indications. The regions 15a and 15b are not discriminated in FIG. 7, but it can be instantly confirmed that the atomic bonds of the two portions are breakable.

Figure 8:
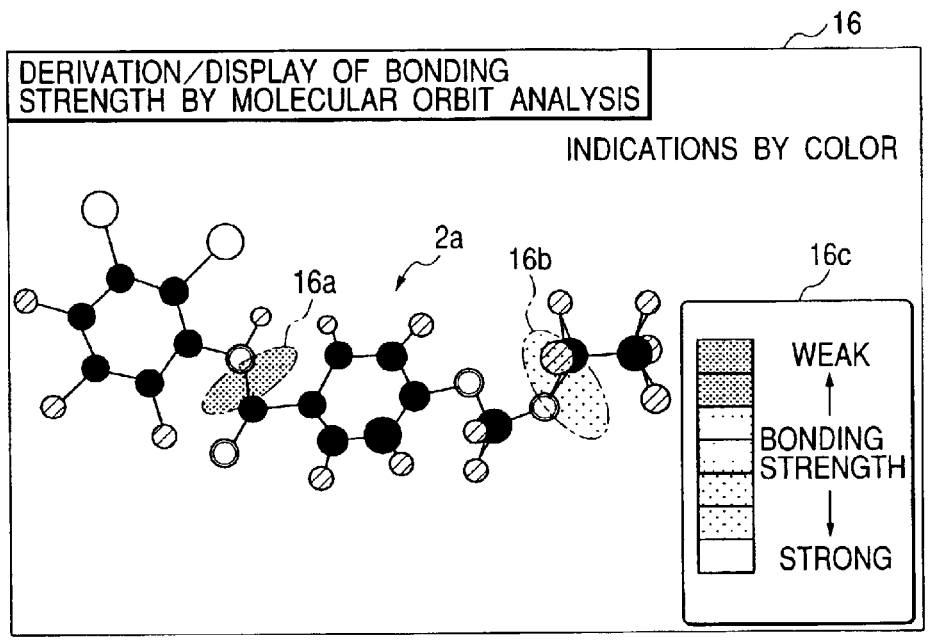
FIG. 8 is a strength indication screen for indicating the analytical result.

In a strength indication screen 16 illustrated in FIG. 8, on the other hand, the regions having lower intermolecular bonding forces are illustrated as regions 16a and 16b in the parent ion candidate 2a, and the regions 16a and 16b are differently colored according to the bonding strengths so that they may be easily discriminated. In this strength indication screen 16, there is arranged a scale 16c indicating the correspondences between the bonding strengths and the colors so that the regions of the lower bonding strengths and their strength relations can be easily confirmed. FIG. 8 illustrates an example indicated at seven stages, which may be differentiated in colors of more or less stages. In one coloring example, the colors are stepwise changed from a red color indicating the weakest bonding through a green color to a blue color indicating a strong bonding, but the coloring may be changed by the section of the user. Moreover, the regions 16a and 16b may be smeared away or may be colored only on contours. The density may be used in place of or together with the smear-away.

Figure 9:
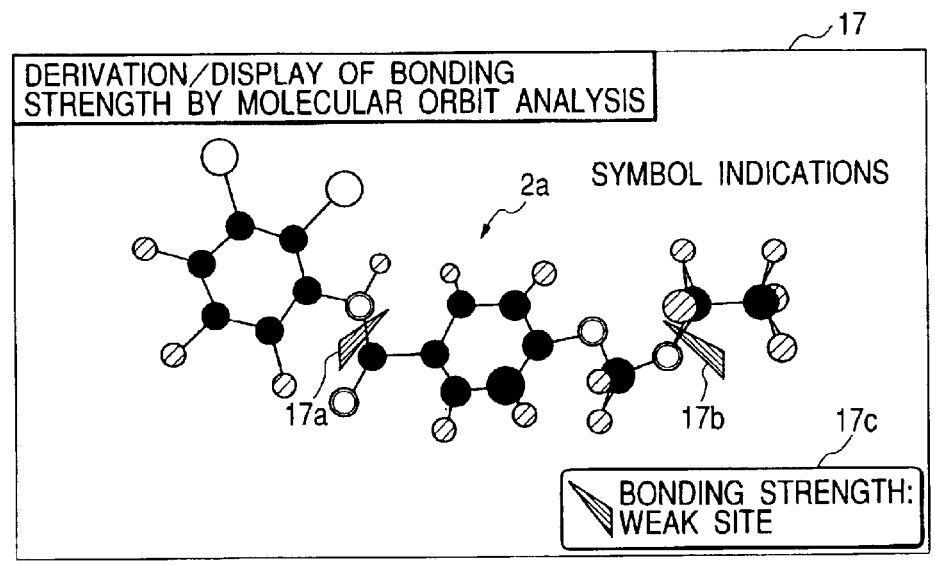
FIG. 9 is a signal indication screen for indicating the analytical result.

FIG. 9 illustrates a symbol indication screen 17 indicating the bonding strength with symbols. For the parent ion candidate 2a, the symbol indication screen 17 contains symbols 17a and 17b attached to atomic bonds of lower bonding strengths, and a text 17c indicating that the bonds bearing the symbols 17a and 17b are portions of weak bonds. According to this symbol indication screen 17, the portions of weak bonds can be instantly confirmed. Here, the symbols 17a and 17b have a triangular shape but may have another polygon or an arrow. By the aforementioned coloring, moreover, the bonding strength can also be confirmed.

In addition to the fact that the structure of the parent ion can be identified highly reliably, according to the present embodiment, there is obtained an effect that the magnitude relations or strengths of the thermal, chemical and energetic properties can be sensed by using the various indications even in case the thermal, chemical and energetic properties obtained by the molecular orbit analysis are invisible if digitally indicated. This effect is prominently exhibited in case the parent ion candidate 2a to be supposed is composed of many atoms.

Here, FIG. 7 to FIG. 9 have only two indication portions, but one or three or more indications may be selected according to the kind of the sample or by the selection of the user. Moreover, the number of ranks to be indicated can also be changed by the selection of the not-shown input means. The ranking indication screen 15 of FIG. 7 and the symbol indication screen 17 of FIG. 9 can attain similar effects even if its indications are made not in the bond-breakable order but in the order of the stronger bonding force. For this case, it is desired that the texts 14b and 17c contain such indications in addition to the information indicating the ranking kind as make it possible to discriminate whether the orders are in the stronger bonding force or in the weaker bonding force.

(Third Embodiment)

A third embodiment of the present invention will be described in detail with reference to the drawings.

The present embodiment is characterized by calculating an activation energy as the thermal, chemical and energetic properties to be derived by the molecular orbit analysis, thereby to derive and display the dissociated ions. The data measurement and processing are done by the mass spectrometer 24 shown in FIG. 1, and the portions to overlap those of the foregoing embodiments will be omitted on their detail description.

The procedure for the parent ion to be dissociated into a plurality of ions will be described from the thermodynamic viewpoints. The parent ion seems to be dissociated after it has transited from a stable state to an active state, and the dissociated ions seem to transit to a stable state. In the present embodiment, therefore, the dissociated ions are derived (at Step S5) by calculating the energy (i.e., the activation energy) necessary for the parent ion to transit to the active state in the molecular orbit analysis of Step S3 of FIG. 2.

Figure 10:
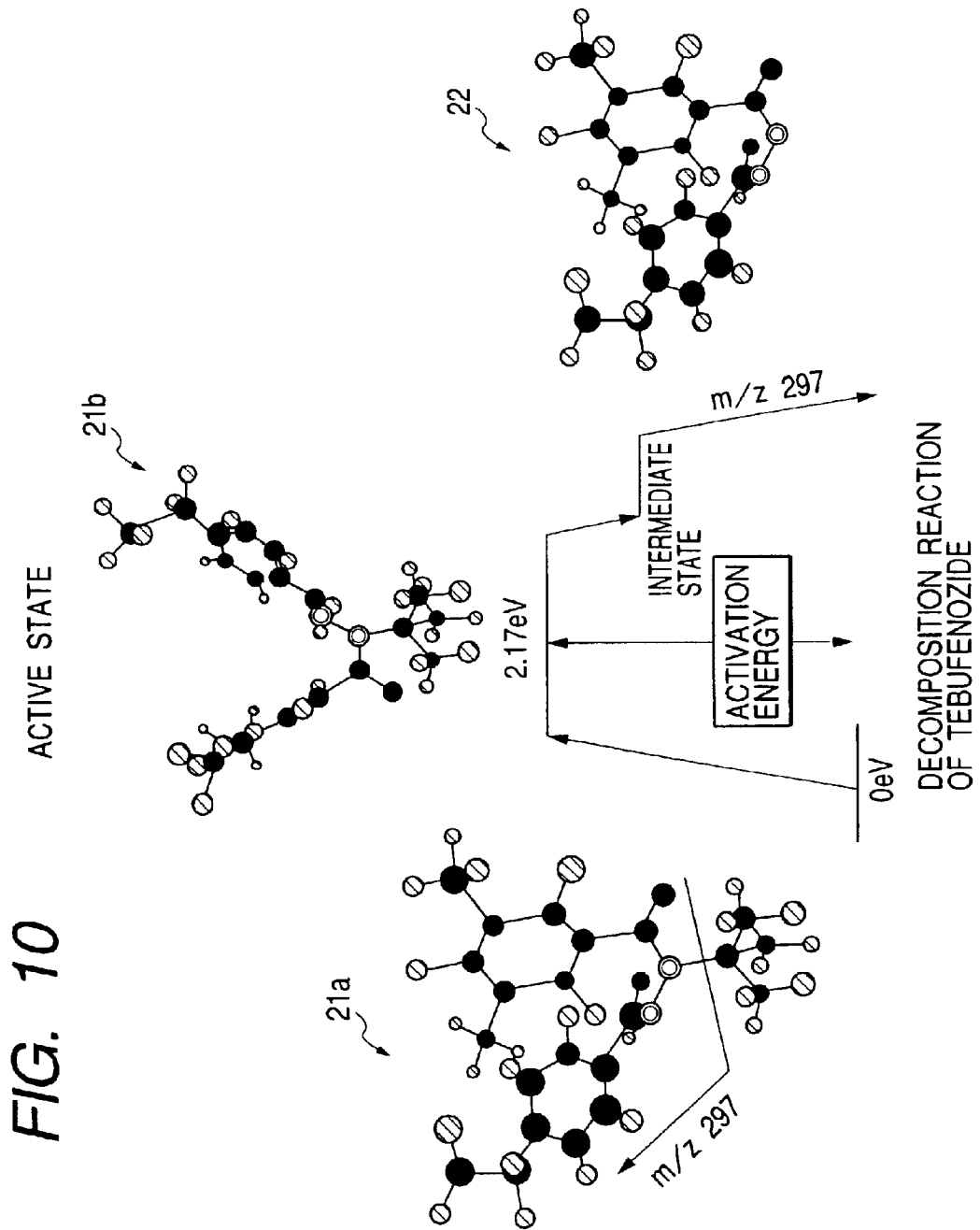
FIG. 10 is a diagram illustrating the dissociation procedures of the sample schematically noting the activation energy.

FIG. 10 illustrates the result that the dissociated species were derived by calculating the energy (or the activation energy) necessary for a pesticide such as tebufenozide to transit actually to the active state by the molecular orbit analysis. The tebufenozide 21a in the stable stage is caused to transit the tebufenozide 21b in the active state by the energy from the outside. The tebufenozide 21b at this time is dissociated, that is, transits to the stabler state or the state of the dissociated ions. The activation energy at this time has a value of 2.17 eV, and the energy from the outside is given by the collision against an inert gas or the irradiation with an infrared ray, for example. The reason why only one dissociated species 22 is illustrated in FIG. 10 is that the ion species measured by the mass spectrometer 24 as the ion species are only the ions of the dissociated species 22 of m/z=297 among the molecules obtained by the dissociative reaction.

Moreover, some substance may have different dissociation procedures for one sample. In other words, different dissociated species may be produced with different activation energies. This case will be described when the parent ion candidate supposed at Step S2 of FIG. 2 is the reserpine 23 having a structure shown in FIG. 11.

The dissociation procedure is examined by analyzing the molecular orbit of the reserpine 23 at Step S3 to calculate the activation energy for the dissociation. The examination reveals the presence of both the dissociation procedure (as indicated at (1) in FIG. 11) to be excited with an energy of about 4 eV and the dissociation procedure (as indicated at (2) in FIG. 11) to be excited with an energy of about 6 eV. Here in the dissociation procedure (1), the C—O—C bonds are broken to produce dissociated species 24a and 24b. When the reserpine 23 is ionized, the atoms located near its center are charged so that the dissociated ion candidate derived at Step S5 is the ions of the dissociated species 24b having an m/z value of 397 amu. In the dissociation procedure (2), on the other hand, the benzene ring is partially broken to produce dissociated species 25a and 25b so that the dissociated species 25b having an m/z value of 448 amu are the dissociated ion candidates.

Figure 11:
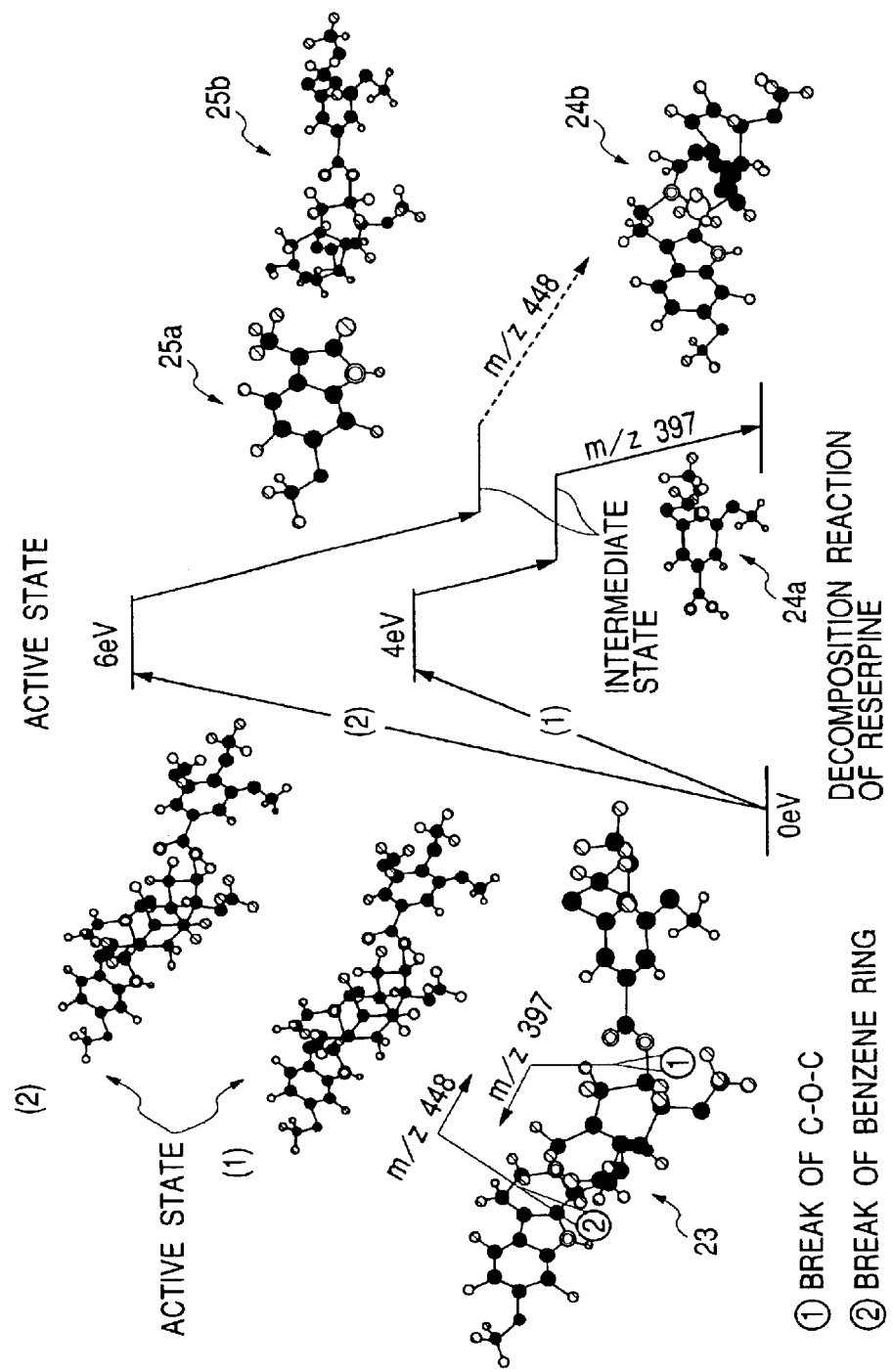
FIG. 11 is a diagram illustrating the dissociation procedures of the sample schematically noting the activation energy.

By thus using the molecular orbit analysis, it is easily understood that a plurality of dissociated species can exist for one sample, and the dissociated species to easily appear can be determined from the magnitude relations of the activation energy. Specifically, it is found that the dissociated species to be produced from the reserpine 23 shown in FIG. 11 are the active species 24b and 25b, and that the ions of the dissociated species 24b obtained through the dissociation procedure (1) of the lower activation energy have a higher probability of detection (or a higher probability of appearance) than that of the ions of the dissociated species 25b obtained through the dissociation procedure (2).

The comparison at Step S7 between the dissociated ion candidate and the mass spectrometric data 1 of the dissociated ions measured actually is made by comparing the mass spectrum made from the m/z value of the dissociated ion candidate and the mass spectrum of the measured dissociated ions.

Figure 12A:
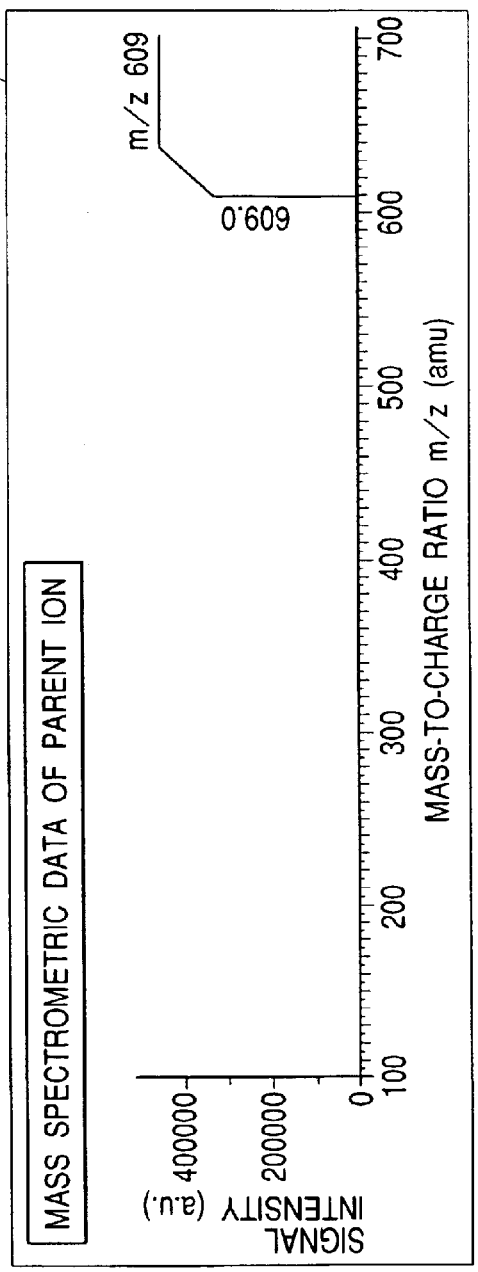
FIG. 12A illustrates the mass spectrometric data of the parent ion measured on reserpine.
Figure 12B:
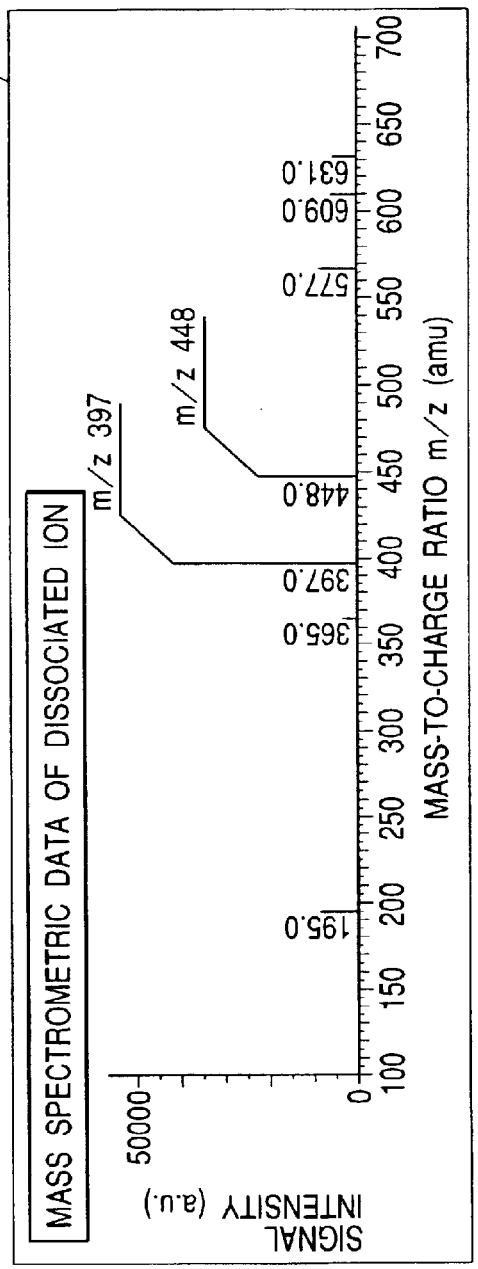
FIG. 12B illustrates the mass spectrometric data of the dissociated ions.

FIG. 12A illustrates the MS data 1a of the sample (having an m/z=609 amu) or the parent ion actually measured, and FIG. 12B illustrates the $MS^2$ data 1b of the dissociated ions of the sample. The results according to FIG. 12B are that the dissociated ions have mass spectrum with peaks at m/z values of 397 amu and 448 amu, and that the dissociated ions having the m/z value of 397 amu have a higher signal intensity than that of the dissociated ions having the m/z value of 448 amu, that is, are more dissociable. This result well coincides with the result of the molecular orbit analysis, as has been described with reference to FIG. 11. From these results, the dissociated ions can be predicted highly precisely to make a high contribution to the supposition of the structure of the parent ion, by calculating and deriving the activation energy by the molecular orbit analysis, by deriving the dissociated ion candidate resultantly, and by estimating the probability of appearance of the candidate.

(Fourth Embodiment)

A fourth embodiment of the present invention will be described in detail.

The present embodiment will be described on the case, in which the molecular orbit is calculated as the thermal, chemical and energetic properties to be derived by the molecular orbit analysis or in which the static potential distribution or the charge distribution in the neutral state is calculated. The data measurement and processing are done by the mass spectrometer 24 shown in FIG. 1, and the portions to overlap those of the foregoing embodiments will be omitted on their detail description.

In the case of calculating the molecular orbit, the highest occupied molecular orbit (HOMO) and the lowest unoccupied molecular orbit (LUMO), and/or the molecular orbits of their peripheries are calculated to judge the bonding states of the entire molecule. Here, the HOMO is the molecular orbit, which is occupied by electrons at the highest energy level, and is an important analytic item for the thermochemical reaction. On the other hand, the LUMO is the molecular orbit, which is occupied by electrons at the lowest energy level, and is an important analytic item for a reaction (e.g., an optically excited reaction) of a slightly higher energy than that of the thermochemical reaction. By calculating the HOMO or LUMO, the unbondably strong portion of the entire molecule can be derived to derive the dissociated species highly precisely. By comparing the m/z values of the dissociated species thus derived with the measured value, moreover, the structure of the parent ion can be supposed highly precisely.

Figure 13:
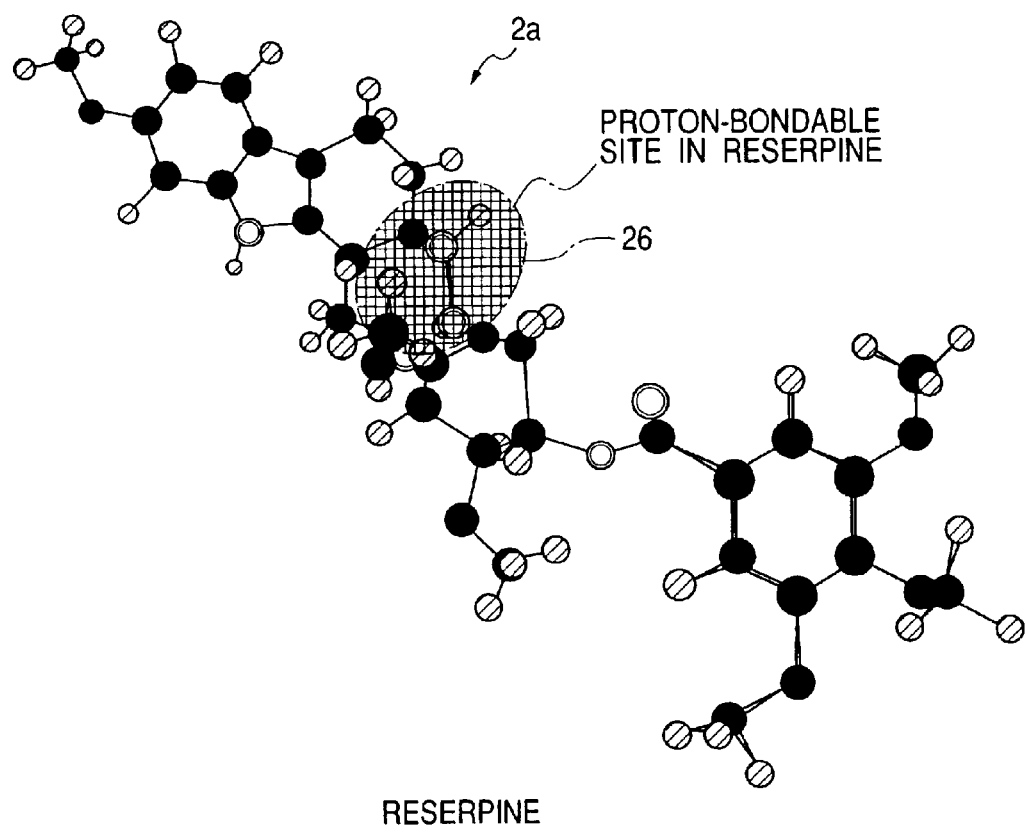
FIG. 13 is a diagram illustrating the most proton-bondable site in the reserpine a really.

When the static potential distribution, the charge distribution in the neutral state or the distribution of the HOMO is to be calculated, on the other hand, it is possible to derive the portion which is easily susceptible to influences at the time of ionizing the parent ion candidate. For example, the portion where the positively charged atoms $H^+$, $Na^+$ or $Li^+$ are the most bondable is derived in the case of the plus ionization, and the portion for the protons to be most dissociable is derived in the case of the minus ionization. FIG. 13 illustrates an example in which the most bondable portion of protons ($H^+$) is displayed as the region 26. According to the present embodiment, the parent ion structure in the ionized state can be supposed to add the influences on the dissociation procedure in the ionized state, so that the dissociated ion candidates can be derived highly precisely. By comparing the m/z values of the dissociated ion candidates thus derived with the mass spectrum of the mass spectrometric data 1*a*measured, moreover, the structure of the parent ion can be supposed highly precisely.

Here, the dissociation procedures, the activation energies, the parent ion candidates 21*a* and 23, the dissociated ion candidates 22, 24*b* and 25*b* and the m/z values, as shown in FIG. 10 and FIG. 11, may be displayed in one screen so that they may be visually grasped by the user. The screens displayed in this case correspond to the parent ion candidate screen (as referred to FIG. 4A) and the analytical result screens 3, 4 and 5 (as referred to FIGS. 4B and 4C and FIG. 5A) in the foregoing embodiments.

The molecular dynamic calculations may be done together with or in place of the molecular orbit calculations. If the molecular dynamic calculations are used, the optimum structure for minimizing the energy can be derived to derive the dissociated ion candidate of a stable structure, i.e., the dissociated ions of a high probability of production (or appearance) as the dissociated ion candidates.

In another method for deriving the dissociated ion candidate by examining the stability, moreover, the energy level in the state after the dissociation may be examined. The dissociated ions at the lower energy level are the stabler so that they can be thought to have a higher probability of appearance. In the case of a plurality of dissociated ion candidates, the dissociated ions can be predicted highly precisely by adding the appearance probability thereby to make a high contribution to the supposition of the structure of the parent ion.

In case the stable state of the dissociated ion candidates is derived, the appearance probability based thereon may be indicated in numerical values. In the case of a plurality of dissociation procedures, the value of the appearance probability may be exemplified by the ratio of the activation energy, the ratio of the energy calculated by the molecular dynamic calculations, or the value converted from the difference in the energy level.

(Fifth Embodiment)

A fifth embodiment of the present invention will be described in detail with reference to the drawings.

Figure 14:
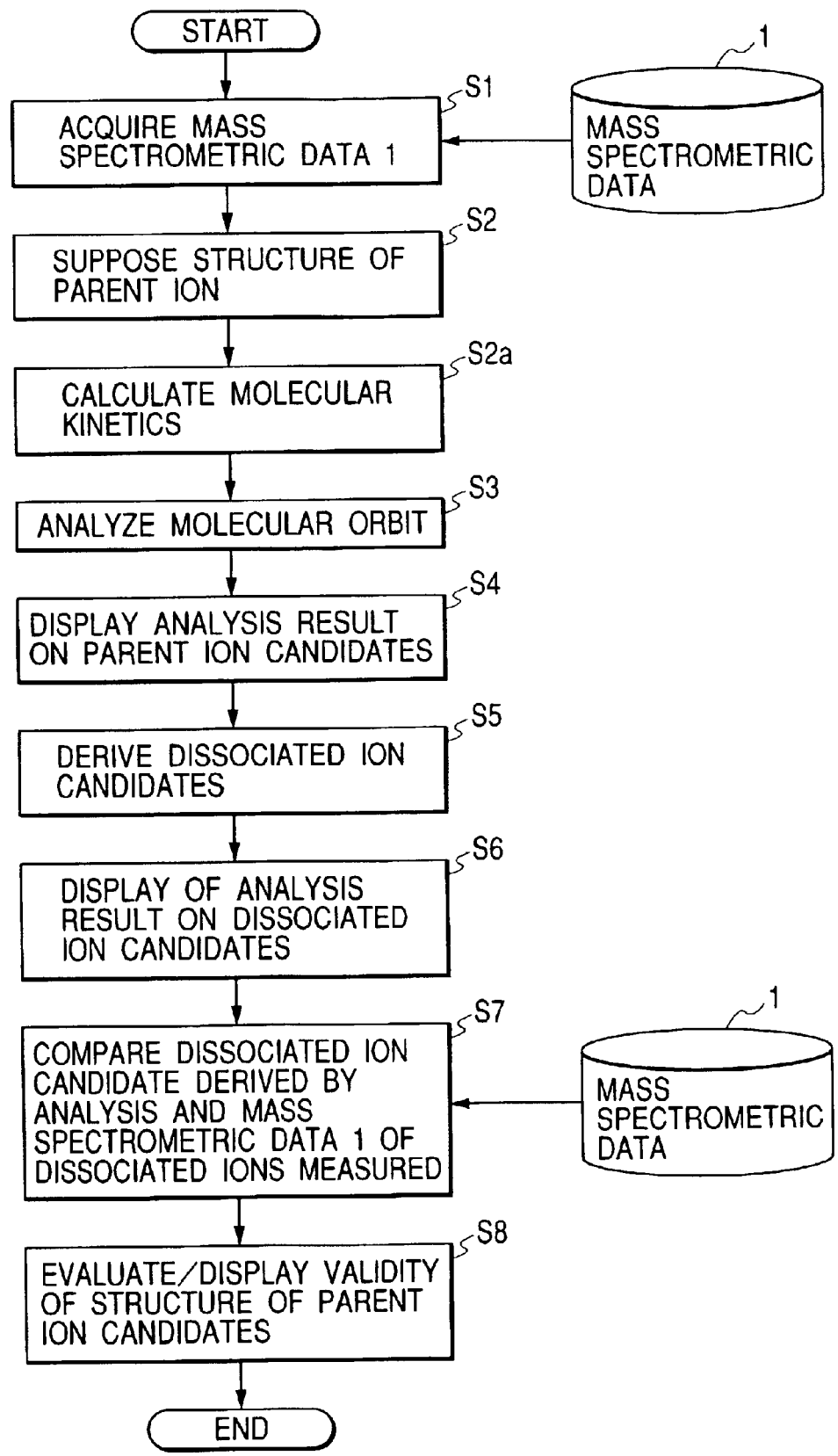
FIG. 14 is a flow chart showing a mass spectrometric data analyzing method.

As shown in FIG. 14, the present embodiment is characterized by deriving the stereoscopic structure of a parent ion by molecular kinetic calculations (at Step S2*a*) before the thermal, chemical and energetic properties are calculated and derived by the molecular orbit analysis (at Step S3) of the parent ion candidate 2*a* having the structure supposed at Step S2. Here, the apparatus construction is identical to that of the mass spectrometer 24 shown in FIG. 1, and the procedure shown in FIG. 14 is also similar but for the molecular kinetic calculations (at Step S2*a*). Therefore, the portions to overlap those of the foregoing individual embodiments will be omitted on their detail description.

Figure 15:
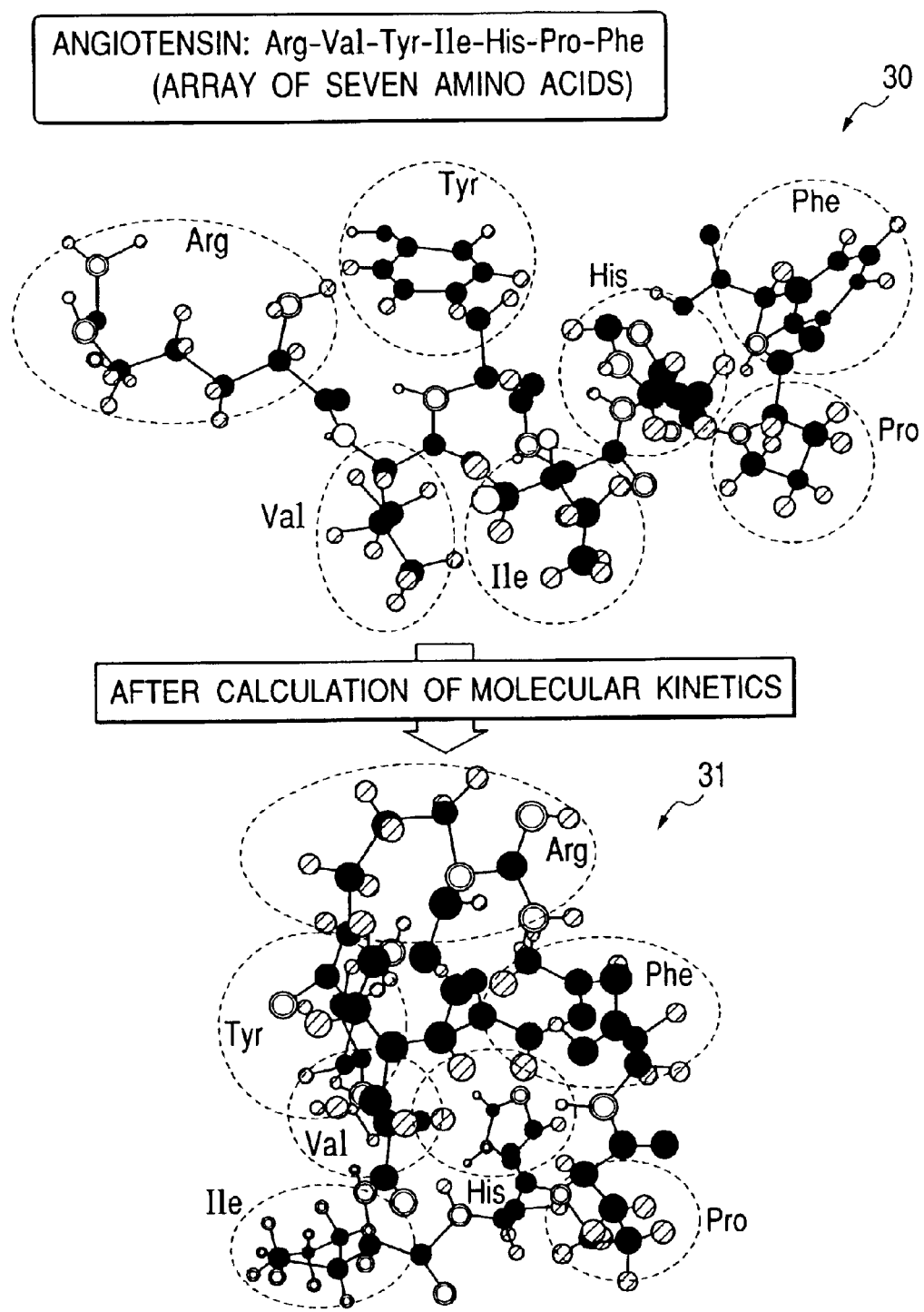
FIG. 15 is a diagram illustrating a structure of angiotensin.

The molecular kinetic calculations to be done at Step S2*a* of FIG. 14 are to calculate the motions of numerous atoms and molecules constructing a substance. These calculations can be used to specify the three-dimensional structure of the sample having a large atomic number such as a high molecule, when the three-dimensional structure is made highly different in the ambient temperature, the properties (e.g., the hydrophobic nature or the hydrophilic nature) of bases constructing the sample or the like. In FIG. 15, here is illustrated a peptide or angiotensin 30 which is constructed of seven amino acid configurations. These seven amino acids are Arg (arginine), Val (valine), Try (tyrosine), Ile (isoleucine), His (histidine), Pro (proline) and Phe (phenylalanine). The angiotensin 30 having such configurations exists in fact as the angiotensin 31 having a circular construction around the hydrophobic base. Thus, the angiotensin 30 of the ideal structure and the angiotensin 31 of the actual structure are so structurally different that they may probably have different dissociable portions. In order to identify the structure of the parent ion highly precisely by deriving the dissociated ion candidate and by comparing it with the $MS^2$ data, specifically, the actual stereoscopic structure of the parent ion candidate used for deriving the dissociated ions is desired to change. Therefore, the parent ion can be identified highly precisely by deriving the stereoscopic structure of the parent ion candidate to be supposed, before the dissociated ions are derived by using the molecular orbit analysis at Step S3.

Thus, the structure of the parent ion can be identified in a high reliability according to the present embodiment. Especially in case the parent ion is a high molecule such as peptide or saccharides, the stereoscopic structure of the parent ion to be supposed can be derived highly precisely to improve the reliability of the dissociated ions derived thereon.

(Sixth Embodiment)

A sixth embodiment of the present invention will be described in detail with reference to the drawings.

Figure 16:
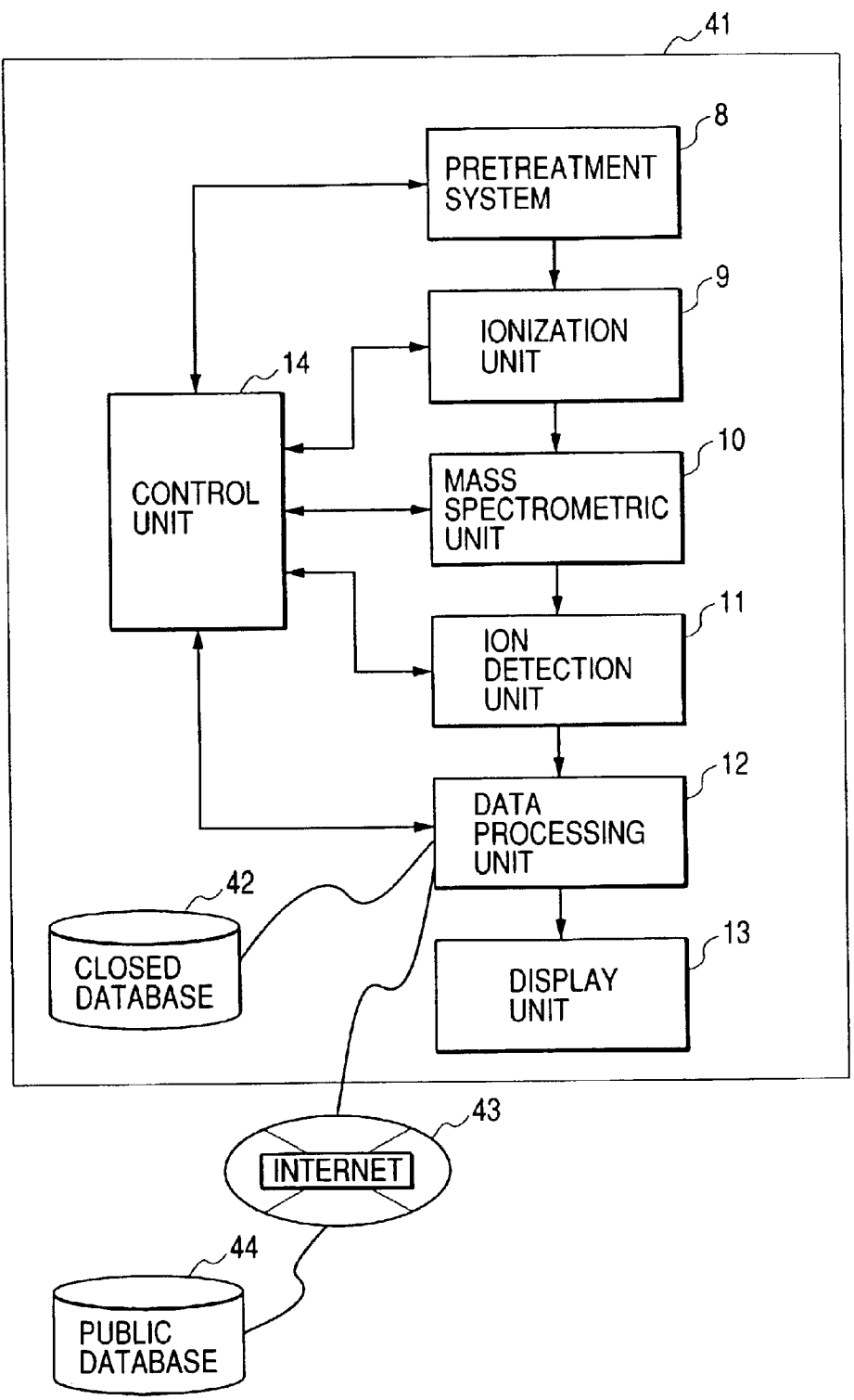
FIG. 16 is a diagram showing a construction of a mass spectrometer or a mass spectrometric data analyzing apparatus.

The present embodiment is characterized in that the mass spectrometry is done by using a mass spectrometer 41 shown in FIG. 16 while utilizing a closed database 42 and a public database 44. This procedure follows a flow chart shown in FIG. 17, and the screen shown in FIG. 18 is provided as one example of the processed result. Here, the portions to overlap those of the foregoing individual embodiments will be omitted on their detail description.

The mass spectrometer 41 or the mass spectrometric data analyzing apparatus is enabled, as shown in FIG. 16, by the data processing unit 12 on the basis of the arranged mass spectrometric data 1 to retrieve the data and to suppose and enumerate the structure of the parent ion by either the closed database 42 owned by the mass spectrometer 41 or the public database 44 which can be accessed to through an internet 43 and opened. The candidates of single or a plurality of parent ion structures, which are supposed and enumerated, can be targeted by the information processing method such as a database retrieving method, a statistical processing method or a numerical arrangement.

Figure 17:
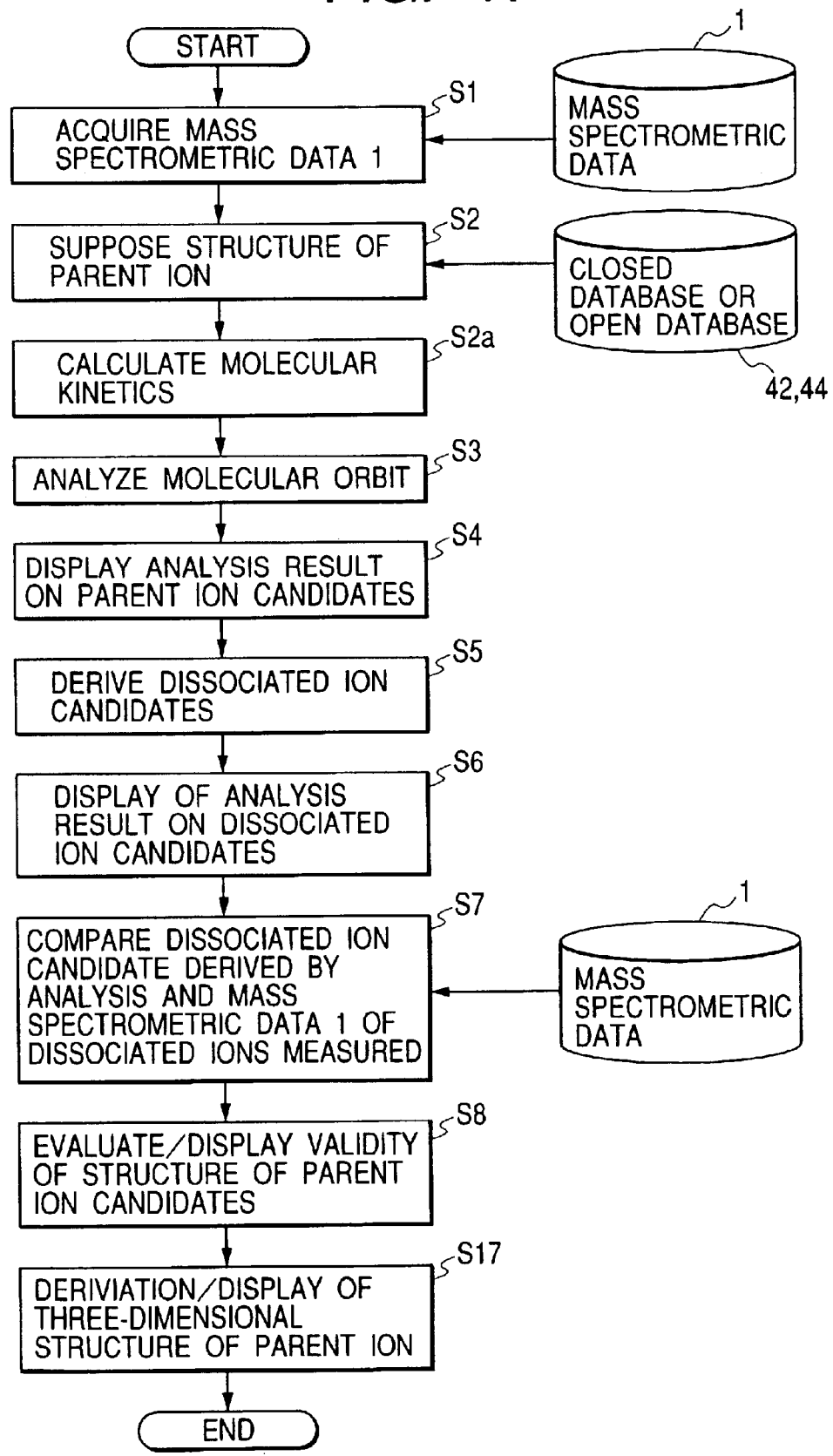
FIG. 17 is a flow chart showing a mass spectrometric data analyzing method.
Figure 18:
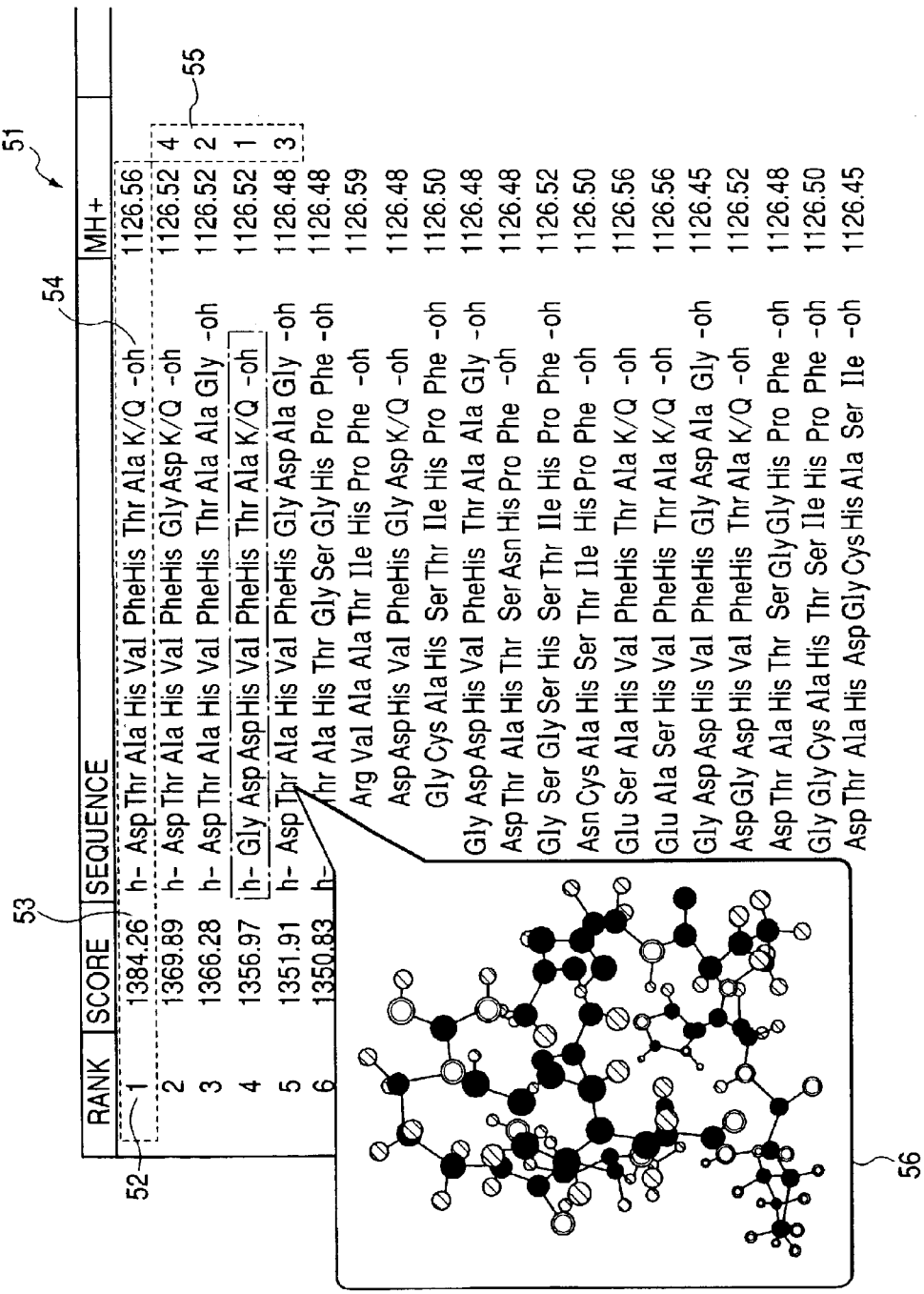
FIG. 18 is a surface screen enumerating the configuration of an amino acid in a table, and a pop-up screen illustrating a three-dimensional structure of a specific configuration.

In the analyzing procedure by the data processing unit 12, the structure of the parent ion is supposed at Step S2 on the basis of the mass spectrometric data 1 acquired at Step S1 of FIG. 17. At this time, there is used the aforementioned closed database 42 or public database 44. Then, at least one of the parent ion candidates obtained by the database retrieval is processed (at Step S2a, Step S3 to Step S8) according to the aforementioned individual embodiments. Then, the validity of the structure of the parent ion supposed at Step S8 is evaluated and displayed, and the three-dimensional structure of the parent ion is derived and displayed at Step S17. Here, the molecular kinetic calculation at Step S2a is not essential but can be omitted.

In connection with an example of FIG. 18, here will be described the screen to be used for supposing the structure of the parent ion at Step S2 and the screen to be used for displaying the three-dimensional structure at Step S17. Here in FIG. 18, a surface screen 51 enumerating the configurations of amino acids in a table and a pop-up screen 56 or a screen illustrating the three-dimensional structure of Step S17 are illustrated as the screen to be displayed at Step S2.

The surface screen 51 includes: a rank column 52 ranking the structures of the parent ion by using the public database 44 and the rules of thumb; a score column 53 indicating the reliabilities of ranks in numerical values; a configuration candidate column 54 indicating the configurations of amino acids; and an analytical result column 55 indicating the ranks made by the molecular orbit analysis. In case the structure is to be supposed from the public database 44 or the like, for example, the amino acid configuration at the first rank of the rank column 52 is the surest structure. From the result of the molecular orbit analysis in the present embodiment, however, it is indicated that the amino acid configuration at the fourth rank in the analytical result column 55 is the most correct structure.

In case numerous candidates are listed up as the parent ion candidates, their reliabilities are usually indicated by scores, which are frequently based on the rules of thumb. Against the rules of thumb, the surest one is finally selected from many candidates by the user on the basis of the expertise. According to the present embodiment, however, even if such many candidates are enumerated, the dissociated ions can be totally derived by the molecular orbit analysis for all the parent ion candidates or the parent ion candidates of a high rank for the correctness. By comparing the result and the mass spectrum of the dissociated ions actually measured, therefore, the consistency or similarity of the two can be derived to evaluate the parent ion structure more precisely. In other words, the parent ion candidates enumerated can be newly ranked on the basis of the result of the molecular orbit analysis. According to the present embodiment, therefore, it is possible to suppose the parent ion structure more precisely or to provide the reliability ranking of the parent ion structure from the viewpoint of the molecular orbit analysis.

On the other hand, the pop-up screen 56 shown in FIG. 18 displays the three-dimensional structure for the parent ion structure at the high rank. With this function, the three-dimensional structure analytical result can be derived from the mass spectrometric result remarkably effectively for the case in which the three-dimensional structure of a synthetic substance or the like is to be confirmed. It is very beneficial that the three-dimensional structure of a drug having a very important meaning in the analysis of its three-dimensional structure can be derived inexpensively and promptly from the mass spectrometric result. Here, FIG. 18 illustrates the three-dimensional structure as the pop-up screen 56 of the surface screen 51, which may be exemplified by another screen to be displayed together with the surface screen 51.

(Seventh Embodiment)

A seventh embodiment of the present invention will be described in detail with reference to the drawings.

Figure 19:
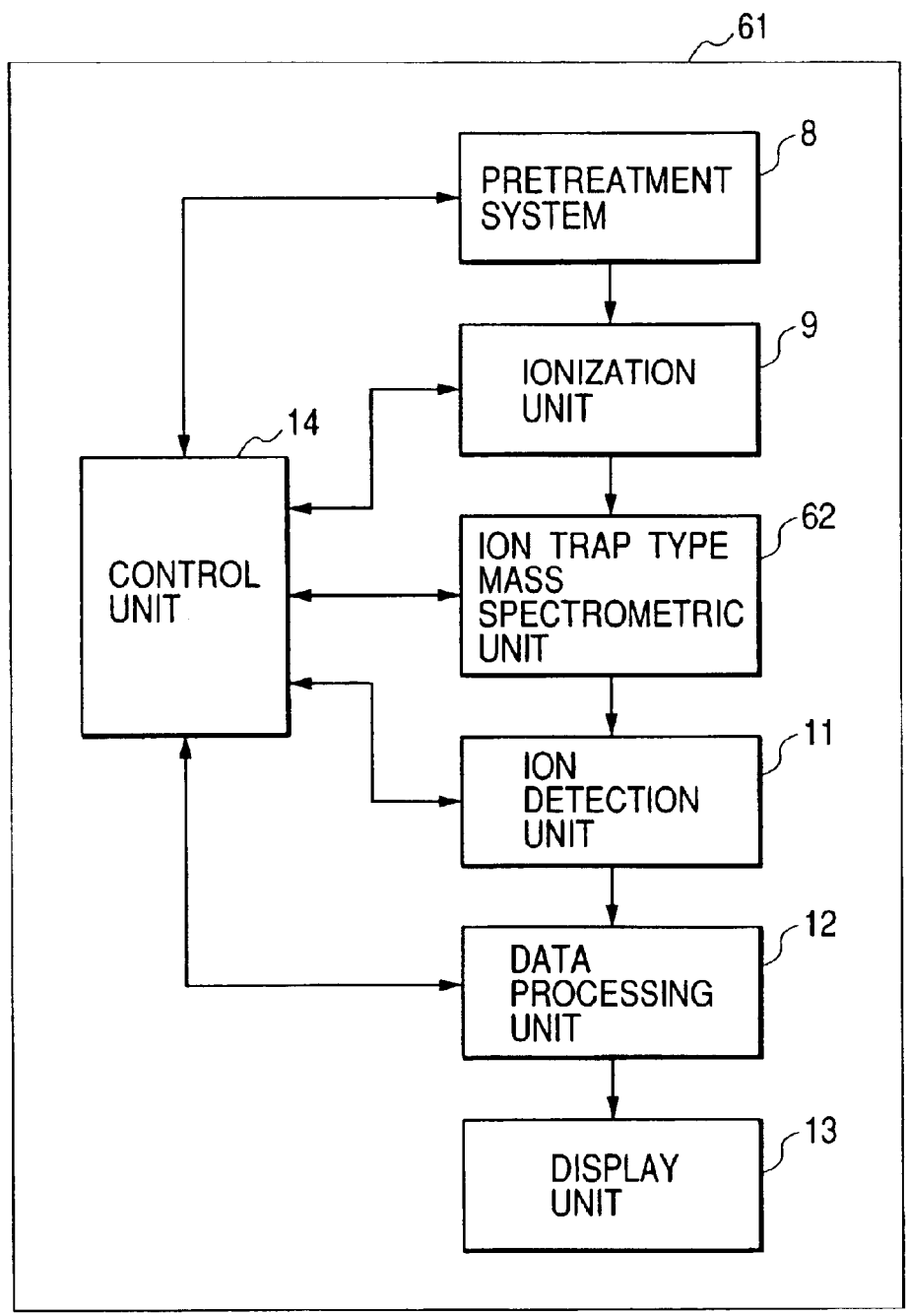
FIG. 19 is a diagram showing a construction of a mass spectrometer or a mass spectrometric data analyzing apparatus.

The present embodiment is characterized by performing the mass spectrometry by using a mass spectrometer 61 shown in FIG. 19. The procedure to be done in this mass spectrometer 61 is followed according to any of FIG. 2, FIG. 14 and FIG. 17 so that its description will be omitted. On the remaining items, the portions to overlap those of the foregoing individual embodiments will be omitted on their detail description.

The mass spectrometer 61 or the mass spectrometric data analyzing apparatus is characterized by including an ion trap type mass spectrometric unit 62 as the mass spectrometric unit. This ion trap type mass spectrometric unit 62 performs the roles of both the mass spectrometric unit 10 shown in FIG. 1 and the not-shown dissociation means. By trapping only the mass-selected parent ion in the ion trap and by applying and superposing the CID (Collision Induced Dissociation) field having a frequency resonant to the parent ion to the ion trap field, the parent ion repeats the collisions against the inert gas filled in the ion trap, so that it is dissociated. The dissociated ions are subjected to the mass spectrometry in the ion trap mass spectrometric unit 62 so that the mass spectrometric data 1 of the parent ion and the dissociated ions are obtained. According to the present embodiment, the ion trap type mass spectrometric unit 62 performs the roles of both the ion dissociation and the mass spectrometry so that the mass spectrometer can be downsized.

(Eighth Embodiment)

An eighth embodiment of the present invention will be described in detail with reference to the drawings.

Figure 20:
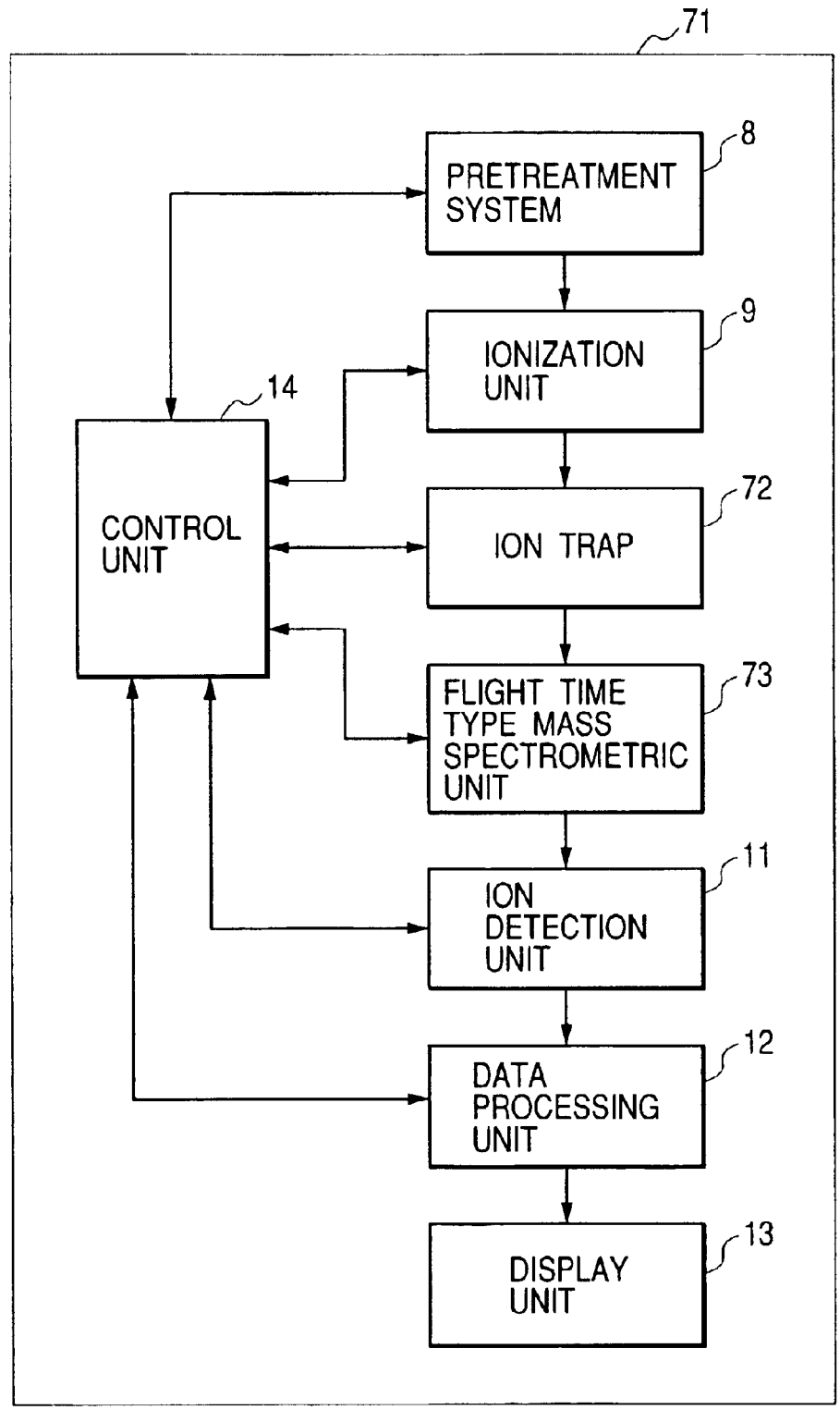
FIG. 20 is a diagram showing a construction of a mass spectrometer or a mass spectrometric data analyzing apparatus.
Figure 21:
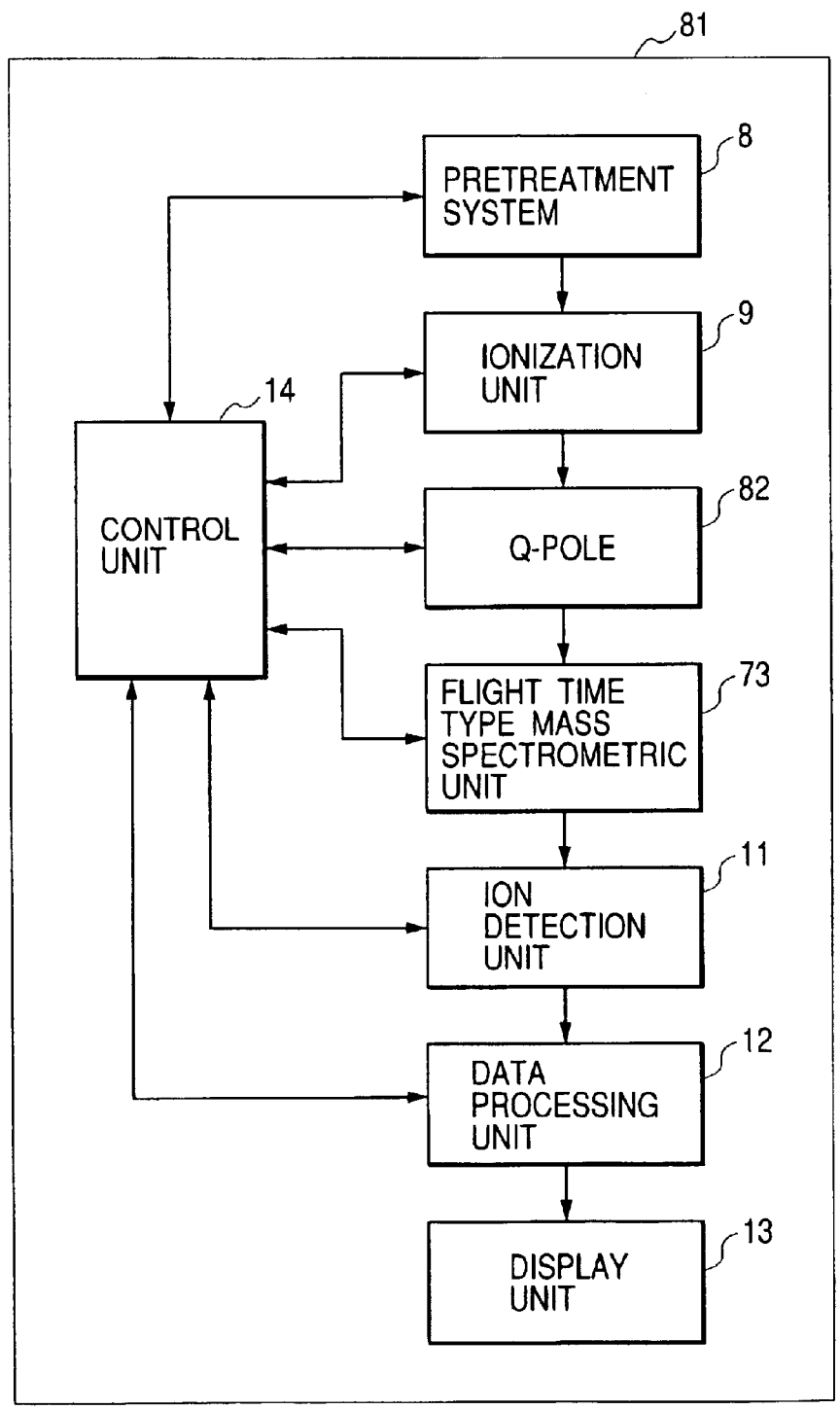
FIG. 21 is a diagram showing a construction of a mass spectrometer or a mass spectrometric data analyzing apparatus.

The present embodiment is characterized in that the mass spectrometry is done by using a mass spectrometer 71 shown in FIG. 20 or a mass spectrometer 81 shown in FIG. 21. Here, the portions to overlap those of the foregoing individual embodiments will be omitted on their detail description.

The mass spectrometer 71 or the mass spectrometric data analyzing apparatus is characterized by including an ion trap 72 as the dissociation means and a Time-Of-Flight type mass spectrometric unit 73 as the mass spectrometric unit, as shown in FIG. 20. This mass spectrometer 71 is optimized, by using the Time-Of-Flight type mass spectrometric unit 73 capable of analyzing a high molecule of a large m/z value, for the case in which a living high molecule is a target for the analysis or in which another high molecule is to be analyzed. As in the mass spectrometer 81 shown in FIG. 21, moreover, a Q-pole 82 having four rod electrodes may be adopted as the dissociation means. As the ions pass through the Q-pole 82 in the atmosphere of a high inert gas pressure, they are trapped to produce the dissociation ions as a result of the collisions against the inert gas. The Q-pole 82 can make the analysis of a higher sensitivity than that of the ion trap so that it is optimized for a microanalysis.

By acquiring the mass spectrometric data using the mass spectrometers 71 and 81 of the present embodiment and by making analyses having been described in the foregoing individual embodiments, the structure of the parent ion, i.e., the sample can be identified highly precisely. Especially by using the mass spectrometer 81, the structure of the parent ion, i.e., the sample can be identified highly precisely even if the target for the analysis is a high molecule such as protein, peptide or saccharides.

(Ninth Embodiment)

A ninth embodiment of the present invention will be described in detail with reference to the drawings.

The present embodiment relates to a solution offering system for performing the analyzing procedure of the foregoing individual embodiments in response to a request from a customer.

Figure 22:
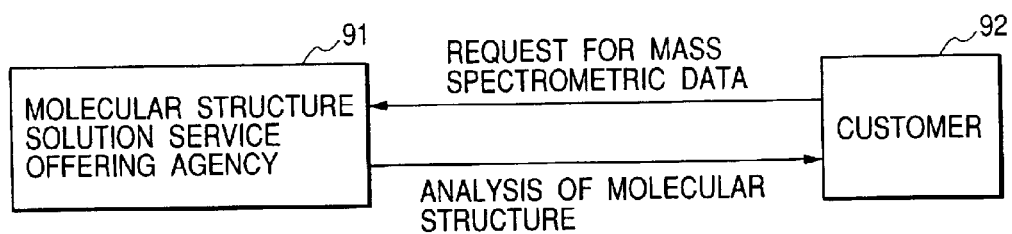
FIG. 22 is a diagram for explaining a solution offering system to be made by using the mass spectrometric data analyzing apparatus of the present invention.

As shown in FIG. 22, the solution offering system is realized by a molecular structure solution service offering agency 91. Experts on molecular orbit analyses and molecular kinetic calculations work at the molecular structure solution service offering agency 91. This agency 91 is constructed to include at least the data processing unit 12 and the display unit 13 (as referred to FIG. 1 and soon) and to output the various analyzing procedures and the outputs of the analytical results in response to the input of the mass spectrometric data 1.

In the solution offering system, the molecular structure solution service offering agency 91 evaluates the parent ion structure in response to a request of a customer 92 for the structure analysis of a sample by the mass spectrometric data analyzing method described in the aforementioned individual embodiments, and offers the finally derived parent ion structure as the solution to the customer. The structure of the parent ion is derived in the molecular structure solution service offering agency 91: by receiving the mass spectrometric data 1 of the parent ion and the dissociated ions, if any, from the customer; by deriving the dissociated ion candidates by the molecular orbit analyses of the parent ion candidates; and by comparing the dissociated ion candidates and the actually measured mass spectrometric data 1 to identify the structure of the parent ion. On the other hand, the customer requests, if having failed to own the mass spectrometric data 1, the agency having the mass spectrometer for the mass spectrometry. On the basis of the data obtained by the agency, the molecular structure solution service offering agency 91 derives the parent ion structure by the mass spectrometric data analyzing method using the molecular orbit analysis, and offers the finally identified parent ion structure to the customer. On the other hand, the molecular structure solution service offering agency 91 receives, if provided with an apparatus such as the mass spectrometer 24 of FIG. 1, a sample in response to a request and performs the mass spectrometry and the analysis of the mass spectrometric data so that it can offer the finally identified parent ion structure to the customer 92.

Upon offer of the solution, the molecular structure solution service offering agency 91 charges the customer 92. The charged sum is varied for the case of only the analysis of the mass spectrometric data or for the case of the additional mass spectrometry, and is determined according to the sample number or the time period for the analysis.

When the request for the structural analysis from the customer 92 is received through the network such as the internet, on the other hand, the offer of the solution or the analytical result or the charge for the offer can also be done through the network.

According to the present embodiment, the experts on the molecular orbit analyses, molecular dynamics and molecular kinetic calculations can be requested for the evaluation/derivation of the parent ion structure so that the result derivations of higher precision and reliability can be expected. Moreover, the work of the customer 92 or the requester can be made efficient by requesting the external agency for the special measurements and the analyzing works.

Moreover, the present invention should not be limited to the aforementioned individual embodiments but could be widely applied.

For example, the mass spectrometric units 10 and 73 of the mass spectrometers 24, 41, 61, 71 and 81 may perform two or more dissociations on the sample. Specifically, the mass spectrometry may be done by dissociating the once dissociated ions produced from the parent ion. In this case, the mass spectrometric data (i.e., $MS^3$ data, $MS^4$ data, - - - , and $MS^n$ data, of which letter n designates a positive integer 3 or more) of the dissociated ions produced by the second and subsequent dissociations can be acquired to provide information on supposition of the structure of a high-molecular sample or the moving state reaction of a medicine. As the data, there may be acquired either: the MS data 1a of the case of no dissociation, as illustrated in FIG. 3A, and the tandem mass spectrometry ($MS^n$: letter n designates an integer of 2 or more) in which the dissociation procedures are done by an arbitrary number of times; or the data of all dissociation stages from the MS data 1a to an arbitrary $MS^n$ data.

In the case of the structural analysis of a sample or such a protein as will acquire the intrinsic function when modified by phosphating it or by adding fatty acid or saccharides, moreover, the modification radicals and the kinds of modifications can be judged by comparing the mass spectrometric data when modified and unmodified, to examine the mass increase due to the modifications. In this case, the mass spectrometry need not be actually done when the mass without the modification can be easily supposed. However, it is also possible to compare the modified sample and the unmodified sample by the individual mass spectrometries, as will be described in the following. When the sample is wholly modified and added, an unmodified sample is prepared by breaking a specific portion of the modified protein with enzymes. Then, the modified sample and the unmodified sample are subjected as the individual parent ions to the mass spectrometry thereby to acquire at least the MS data and the $MS^2$ data. On the unmodified parent ion, the data processing unit 12 analyzes the structure in accordance with the aforementioned individual embodiments and compares the MS data of the two parent ions thereby to specify the modifying radicals. At this time, it is desired to examine whether or not the modifying radicals are bonded to the dissociated ions, too, by comparing the corresponding $MS^2$ data. The analytical results are displayed in the display unit 13. The display scan be exemplified by the structure of the sample containing the modifying radicals and/or the structure of the dissociated ions containing the modifying radicals.

In another mode of the solution offering service to be done in the ninth embodiment, moreover, the database of the $MS^n$ data, which has been derived by the molecular orbit calculations from the molecular structure solution service offering agency 91, is offered to the customer 92. This database has a structure in which the names, the m/z values, the structures and the physical properties of samples and bases described in the aforementioned individual embodiments are so configured at least partially that they can be retrieved.

Moreover, it is also contained in the execution of the present invention to analyze the structure of the sample by causing a computer having at least data processing function to start the analyzing program for the analyzing procedures described in the aforementioned individual embodiments, and to record such analyzing program in a recording medium such as the CD-ROM or to transmit the program through the network.

According to the present invention, it is possible to derive the structure of a sample highly precisely. By offering the result and the grounding for the derivation by a screen display, moreover, it is possible to confirm and utilize the analytical result efficiently.

What is claimed is:

1. An analyzing apparatus comprising a data processing unit and a display unit and used for analyzing the structure of an ionized sample on the basis of the mass spectrometric data measured on said sample and the mass spectrometric data measured on dissociated ions obtained by cleaving said sample as a parent ion, wherein said data processing unit includes constructions: to analyze parent ion candidates; and to analyze the structure of said parent ion by comparing the analytical result of the parent ion candidates and the mass spectrometric data of the dissociated ions measured; and said display unit includes a construction to display the analytical result of the structure of said parent ion.

2. A mass spectrometric data analyzing apparatus as set forth in claim 1, wherein the display of said analytical result is made with the values of the calculated properties in absolute or relative values.

3. A mass spectrometric data analyzing apparatus as set forth in claim 1, wherein the display of said analytical result is made with the numerical values ranking the calculated properties in relation to the structure of said parent ion candidate.

4. A mass spectrometric data analyzing apparatus as set forth in claim 1, wherein the display of said analytical result includes at least one of distribution indication, indication by color and density indication correlating the calculated properties and the structurally specific portions of said parent ion candidates.

5. A mass spectrometric data analyzing apparatus as set forth in claim 1, wherein the display of said analytical result is made by attaching symbols relating to the magnitude of the calculated properties, to the structure of said parent ion candidates.

6. A mass spectrometric data analyzing apparatus as set forth in claim 1, wherein the display of said analytical result contains the indication of the structure of the parent ion candidates derived.

7. A mass spectrometric data analyzing apparatus as set forth in claim 1, wherein the display of said analytical result is a mass spectrum prepared corresponding to the magnitude of the appearance probability of the dissociated ion candidates derived.

8. A mass spectrometric data analyzing apparatus as set forth in claim 1, wherein the display of said analytical result contains said mass spectra of said dissociated ion candidates and the mass spectra of the dissociated ions contained in the measured mass spectrometric data, in an overlapping manner or in parallel.

9. A mass spectrometric data analyzing apparatus as set forth in claim 1, wherein the display of said analytical result attaches the stability of the dissociated ion candidates derived, to the structure of said dissociated ion candidates.

10. A mass spectrometric data analyzing apparatus as set forth in claim 1, wherein the display of said analytical result contains the procedure for appearance of the derived dissociated ion candidates, together with the calculated properties.

11. A mass spectrometric data analyzing apparatus as set forth in claim 1, wherein the display of said analytical result contains the consistency percentage or the difference percentage between the mass spectra of the dissociated ion candidates derived and the mass spectra of the dissociated ions contained in the mass spectrometric data measured.

12. A mass spectrometric data analyzing apparatus as set forth in claim 1, wherein a three-dimensional structure is indicated of at least one of said parent ion candidates ranked.

13. A mass spectrometric data analyzing apparatus as set forth in claim 1, wherein said data processing unit derives the kind and structure of the modifying radicals modifying and added to the parent ion, on the basis of the comparison result between the mass spectra of said dissociated ion candidates and the measured dissociated ions so that the derivation result is displayed by said display unit.

14. A solution offering system for offering to a customer the identification of a substance requested by the customer or the evaluation result of a three-dimensional structure as a solution by using a mass spectrometric data analyzing system as set forth in claim 1.

15. A program for analyzing mass spectrometric data for causing a computer to function as:

means for acquiring the mass spectrometric data measured on an ionized sample and the mass spectrometric data measured on the dissociated ions obtained by cleaving said sample as a parent ion;

means for calculating at least one of the thermal, chemical energetic properties on the candidates of said parent ion supposed from said mass spectrometric data acquired, to derive the parent ion candidates and the structure of the dissociated ions as the dissociated ion candidates, and for comparing the mass spectra of the derived dissociated ion candidates and the measured dissociated ions, to analyze the structure of said parent ion; and means for displaying the analytical result of at least the structure of said parent ion.

* * * * *